US009034870B2

(12) United States Patent
Cushman et al.

(10) Patent No.: US 9,034,870 B2
(45) Date of Patent: *May 19, 2015

(54) AZAINDENOISOQUINOLINE TOPOISOMERASE I INHIBITORS

(71) Applicants: Purdue Research Foundation, West Lafayette, IN (US); United States Government National Institutes of Health (NIH), U.S. Dept. of Health and Human Services (DHHS), Washington, DC (US)

(72) Inventors: Mark S. Cushman, West Lafayette, IN (US); Evgeny A. Kiselev, Silver Spring, MD (US); Andrew E. Morrell, San Diego, CA (US); Yves George Pommier, Bethesda, MD (US)

(73) Assignees: Purdue Research Foundation, West Lafayette, IN (US); United States Government National Institutes of Health (NIH), U.S. Dept. of Health and Human Services (DHHS), NIH Division of Extramural Inventions and Technology Resources (DEITR), Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/199,754

(22) Filed: Mar. 6, 2014

(65) Prior Publication Data

US 2014/0187547 A1    Jul. 3, 2014

Related U.S. Application Data

(63) Continuation-in-part of application No. 13/548,579, filed on Jul. 13, 2012, now Pat. No. 8,686,146.

(60) Provisional application No. 61/906,223, filed on Nov. 19, 2013.

(51) Int. Cl.
*C07D 471/04* (2006.01)

(52) U.S. Cl.
CPC .................................. *C07D 471/04* (2013.01)

(58) Field of Classification Search
None
See application file for complete search history.

(56) References Cited

U.S. PATENT DOCUMENTS

| | | | |
|---|---|---|---|
| 3,536,809 | A | 10/1970 | Applezweig |
| 3,598,123 | A | 8/1971 | Zaffaroni |
| 3,630,200 | A | 12/1971 | Higuchi |
| 3,847,770 | A | 11/1974 | Radlowe et al. |
| 3,916,899 | A | 11/1975 | Theeuwes et al. |
| 4,008,719 | A | 2/1977 | Theeuwes et al. |
| 4,687,610 | A | 8/1987 | Vassilatos |
| 4,769,027 | A | 9/1988 | Baker et al. |
| 5,059,595 | A | 10/1991 | Le Grazie |
| 5,073,543 | A | 12/1991 | Marshall et al. |
| 5,120,548 | A | 6/1992 | McClelland et al. |
| 5,354,566 | A | 10/1994 | Addesso et al. |
| 5,591,767 | A | 1/1997 | Mohr et al. |
| 5,597,831 | A | 1/1997 | Michalsky et al. |
| 5,639,476 | A | 6/1997 | Oshlack et al. |
| 5,674,533 | A | 10/1997 | Santus et al. |
| 5,733,566 | A | 3/1998 | Lewis |
| 6,509,344 | B1 | 1/2003 | Cushman et al. |
| 7,312,228 | B2 | 12/2007 | Cushman et al. |
| 7,495,100 | B2 | 2/2009 | Cushman et al. |
| 7,781,445 | B2 | 8/2010 | Cushman et al. |
| 8,053,443 | B2 | 11/2011 | Cushman et al. |
| 2004/0229895 | A1 | 11/2004 | Jagtap et al. |
| 2008/0262016 | A1 | 10/2008 | Jagtap et al. |
| 2008/0318995 | A1 | 12/2008 | Cushman et al. |
| 2012/0302563 | A1 | 11/2012 | Cushman et al. |

FOREIGN PATENT DOCUMENTS

| | | |
|---|---|---|
| WO | WO 2004/014862 | 2/2004 |
| WO | WO 2012/024437 | 2/2012 |
| WO | WO 201 2/1 6251 | 11/2012 |

OTHER PUBLICATIONS

Wawzonek et al., 17(2) Organic Preparations. & Procedures International 115-20 (1985) (CAS Abstract).*
Alfonso et al. "Analogues of 1-(3,10-Dibromo-8-chloro-6,11-dihydro-5H-benzo[5,6]-cyclohepta[1,2-b]pyridin-11-y1)piperidine as inhibitors of farnesyl protein transferase", Bioorganic & Medicinal Chemistry, vol. 7, Issue 9, Sep. 1999, pp. 1845-1855.
Antony et al., "Differential Induction of Topoisomerase I-DNA Cleavage Complexes by the Indenoisoquinoline MJ-III-65 (NSC 706744) and Camptothecin: Base Sequence Analysis and Activity against Camptothecin-Resistant Topoisomerase I," Cancer Res., 2003, 63, 7428-7435.
Antony et al., "Cellular Topoisomerase I Inhibition and Antiproliferative Activity by MJ-III-65 (NSC 706744), an Indenoisoquinoline Topoisomerase I Poison," *Molecular Pharmacology*, 2005, vol. 67, No. 2, 523-530.
Bobbitt et al. "Synthesis of Isoquinoline Alkaloids. II. The Synthesis and Reactions of 4-Methyl-3-pyridinecarboxaldehyde and Other 4-Methyl-3-substituted Pyridines1,2", *J. Org. Chem.*, 1960, 25 (4), pp. 560-564.
Boyd et al. "some practical considerations and applications of the national cancer institute in vitro anticancer drug discovery screen", Feb. 1995, Drug Development Research, vol. 34, issue 2, pp. 91-109.

(Continued)

*Primary Examiner* — Timothy R Rozof
(74) *Attorney, Agent, or Firm* — Mark S. Cohen; Pearl Cohen; Zedek Latzer Baratz LLP

(57) ABSTRACT

The invention described herein pertains to substituted azaindenoisoquinoline compounds, in particular 7-, 8-, 9-, and 10-azaindenoisoquinoline compounds, which are inhibitors of topoisomerase I, processes and intermediates for their syntheses, pharmaceutical compositions of the compounds, and methods of using them in the treatment of cancer.

18 Claims, No Drawings

(56) References Cited

OTHER PUBLICATIONS

Chen et al.; Acridone-based inhibitors of inosine 50—monophosphate dehydrogenase: Discovery and SAR leading to the identification of N-(2-(6-(4-ethylpiperazin-111)pyridine-3-Apropan-211)-2-fluoro-9-oxo-9,10-dihydroacridine-3-carboxamide (BMS-566419). J. Med.

Clarke et al.; "Preparation of some thiopyranopyridine derivatives", J. Chem. Soc. Perkin. Trans., 1 1984, 1501-1505.

Cushman, Mark, Prem Mohan, and Edward CR Smith. "Synthesis and biological activity of structural analogs of the anticancer benzophenanthridine alkaloid nitidine chloride." Journal of medicinal chemistry 27.4 (1984): 544-547.

Cushman, Mark, et al., "Synthesis of a New Indeno[1,2-c]Isoquinolines: Cytotoxic Non-Camptothecin Topoisomerase I Inhibitors," 2000, Journal of Medicinal Chemistry, vol. 43, No. 20, pp. 3688-3698.

Cushman, Mark, and Prem Mohan. "Synthesis and antitumor activity of structural analogs of the anticancer benzophenanthridine alkaloid fagaronine chloride." Journal of medicinal chemistry 28.8 (1985): 1031-1036.

Danks, M.K.; Pawlik, C.A.; Whipple, D.O.; Wolverton, J.S., Intermittant Exposure of Medulloblastoma Cells to Topotecan Produces Growth Inhibition equivalent to Continuous Exposure, Clinical Cancer Research, 1997, 3, 1731-1738.

Das et al. "A facile nuclear bromination of phenols and anilines using NBS in the presence of ammonium acetate as a catalyst", Journal of Molecular Catalysis A: Chemical, vol. 267, Issues 1-2, Apr. 18, 2007, pp. 30-33.

Dexheimer et al. "DNA cleavage assay for the identification of topoisomerase I inhibitors", 2008, Nature Protocols vol. 3 No. 11, pp. 1736-1750.

Freireich et al., "Quantitative Comparison to Toxicity of Anticancer Agents in Mouse, Rat, Hamster, Dog, Monkey, and Man," Cancer Chemother. Rep., 1966, 50 (4), 219-244.

Haas, N. B.; LaCreta, F.P.; Walczak, J.; Hudes, G.R.; Brennan, J.M.; Ozols, R.F.; O'Dwyer, P.J. "Phase 1/Pharmacokinetic Study of Topotecan by 24-Hour Continuous Infusion Weekly," *Cancer Res.*, 1994, 54, 1220-1226.

Hollingshead et al. "The Hollow Fiber Assay," Contrib. Oncol, 109-120 ,1999, 54.

Ioanoviciu et al. "Synthesis and Mechanism of Action Studies of a Series of Norindenoisoquinoline Topoisomerase I Poisons Reveal an Inhibitor with a Flipped Orientation in the Ternary DNA-Enzyme—Inhibitor Complex As Determined by X-ray Crystallographic Analysis" *J. Med. Chem.*, 2005, vol. 48, No. 15, 4803-4814.

Jaxel et al. "Structure-Activity Study of the Actions of Camptothecin Derivatives on Mammalian Topoisomerase I: Evidence for a Specific Receptor Site and a Relation to Antitumor Activity," *Cancer. Rev.*, 1989, 49, 1465-1469.

Jayaraman et al. "Synthesis of New Dihydroindeno[l-2-c]lsoquinolone and Indenoisoquinolinium Chloride Topoisomerase I Inhibitors Having High in Vivo Anticancer Activity in the Hollow Fiber Animal Model", 2002, Journal of Medicinal Chemistry, vol. 45, No. 1, pp. 242-249.

Khanna et al. "Selective Cyclooxygenase-2 Inhibitors: Heteroaryl Modified 1,2-Diarylimidazoles Are Potent, Orally Active Antiinflammatory Agents", *J. Med. Chem.*, 2000, 43 (16), pp. 3168-3185.

Kiselev et al. "7-azaindenoisoquinolines as topoisomerase I inhibitors and potential anticancer agents." *Journal of medicinal chemistry* 54.17 (2011): 6106-6116.

Kiselev et al. "Azaindenoisoquinolines as Topoisomerase 1 Inhibitors and Potential Anticancer Agents: A Systematic Study of Structure-Activity Relationships." *Journal of medicinal chemistry* 55.4 (2012): 1682-1697.

Kohlhagen et al. "Protein-Linked DNA Strand Breaks Induced by NSC 314622, a Novel Noncamptothecin Topoisomerase I Poison" *Mol. Pharmacol.*, 1998, 54, 50- 58.

Kucerova et al. "Solovolysis of 0-acyl-10-hydroxy-10-dihydro-indeno[1,2-c]lsoquinolin—5,11-diones", 1979, Database CA, Chemical Abstracts Service, Database Accession No. 1980:22814.

Minami et al. "Limited Sampling Model for the Area under the Concentration Time Curve of Total Topotecan," *Clin. Cancer Res.*, 1996, 2, 43-46.

Morrell et al. "Synthesis, of Nitrated Indenoisoquinolines as Topoisomerase I Inhibitors," 2004, *Bioorganic & Medicinal Chemistry Letters*, vol. 14, pp. 3659-3663.

Nagarajan et al. "Synthesis and Anticancer Activity of Simplified Indenoisoquinoline Topoisomerase I Inhibitors Lacking Substituents on the Aromatic Ring,5'", 2004, Journal of Medicinal Chemistry, vol. 47, No. 23, pp. 5651-5661.

Nagarajan et al. "Design, Synthesis, and Biological Evaluation of Indenoisoquinoline Topoisomerase I Inhibitors Featuring Polyamine Side Chains on the Lactam Nitrogen" J. Med. Chem,. 2003, 46, 5712-5724.

Pailer et al. "Some reactions of 2-aryl-1,3-indandiones," *Monatsh Chem.*, 1961, 92, 1037-1047.

Peterson et al. "Alcohol-, Diol-, and Carbohydrate-Substituted Indenoisoquinolines as Topoisomerase I Inhibitors: Investigating the Relationships Involving Stereochemistry, Hydrogen Bonding, and Biological Activity." *Journal of medicinal chemistry* 54.14 (2011): 4937-4953.

Plowman et al. "US NCI Testing Procedures," Contrib. Onco, l. 1999, 54, 121-135.

Pommier et al. "Mechanism of Action of Eukaryotic DNA Topoisomerase I and Drugs Targeted to the Enzyme," *Biochim. Biophys. Acta*, 1998, 1400, 83-106.

Pourquier et al. Induction of Reversible Complexes between Eukaryotic DNA Topoisomerase I and DNA-containing Oxidative Base Damages 7,8-Dihydro-8-0xoguanine and 5-Hydroxycytosine, Mar. 26, 1999, The Journal of Biological Chemistry, 274, 8516-8523.

Shapiro et al. "Indandiones. II. A Modified Dieckmann Reaction," *J. Org. Chem.*, 1961, 26, 3580-3582.

Skehan et al. "New Colorimetric Cytotoxicity Assay for Anticancer-Drug Screening", J Natl Cancer Inst (1990) 82 (13): 1107-1112.

Staker et al. "Structures of Three Classes of Anticancer Agents Bound to the Human Topoisomerase I-DNA Covalent Complex," J. Med. Chem., 2005, vol. 48, No. 7, 2336-2345.

Staker et al. "The Mechanism of Topoisomerase I Poisoning by a Camptothecin Analog," *Proc. Natl. Acad. Sci. U.S.A.*, 2002, 99, 15387-15392.

Strumberg et al., "Synthesis of Cytotoxic Indenoisoquinoline Topoisomerase I Poisons," 1999, Journal of Medicinal Chemistry, vol. 42, No. 3, pp. 446-457.

Van Der Does et al. "Bromination of methylpyridines in fuming sulfuric acid", Recueil des Travaux Chimiques des Pays-Bas vol. 84, Issue 7, pp. 951-964, 1965.

Vogel, editor "Drug Discovery and Evaluation: Safety and Pharmacokinetic Assays", 2006, Springer Publishers, pp. 400-402.

Wawzonek "Novel Formation of 1 I-Ketoindeno[1,2-c]lsocoumarin," 1968, The Journal of Organic Chemistry, vol. 33, No. 2, pp: 896-897.

Wawzonek "Synthesis of 6-Substituted-6H-Indeno[1,2-c] Isoquinoline-5,11-diones," 1982, Database CA, Chemical Abstracts Service, Database Accession No. 1982:199485.

Wawzonek et al. "The Synthesis and Reactions of 1-Carbamyl-1 1-ketoindeno [1,2-c] isoquinolinel." The Journal of Organic Chemistry 31.4 (1966): 1004-1006.

West "Solid State Chemistry and its Applications," Wiley, New York, 1988, pp. 358 & 365.

Xiao et al., "On the Binding of Indeno[1,2-c]isoquinolines in the DNA-Topoisomerase I Cleavage Complex," J. Med. Chem., 2005, vol. 48, No. 9, 3231-3238.

* cited by examiner

AZAINDENOISOQUINOLINE TOPOISOMERASE I INHIBITORS

RELATED APPLICATIONS

The present application is a continuation-in-part of U.S. nonprovisional application Ser. No. 13/548,579, filed Jul. 13, 2012, and also claims priority to and incorporates U.S. provisional patent application Ser. No. 61/906,223 filed Nov. 19, 2013, the content of each of which is incorporated by reference herein in its entirety.

GOVERNMENT RIGHTS

This invention was made with government support under CA089566 awarded by the National Institutes of Health. The government has certain rights in the invention.

TECHNICAL FIELD

The invention described herein pertains to substituted azaindenoisoquinoline compounds, in particular 7-, 8-, 9-, and 10-azaindenoisoquinoline compounds, which are inhibitors of topoisomerase I, processes and intermediates for their syntheses, pharmaceutical compositions of the compounds, and methods of using them in the treatment of cancer.

BACKGROUND AND SUMMARY OF THE INVENTION

Human topoisomerase type I (Top1) is a ubiquitous cellular enzyme. It is a member of the topoisomerase family of enzymes that solve DNA topological problems associated with supercoiling. DNA supercoiling occurs during a number of vital cellular processes such as replication, transcription, and DNA repair. Top1 relaxes DNA by producing reversible single-strand DNA cuts. The generally accepted mechanism of Top1 action involves formation of a covalent link between the catalytic tyrosine 723 residue of Top1 and the 3'-end of the cut DNA strand in the Top1-DNA cleavage complex (Top1-DNAcc). The rotation of the 5'-end around the intact strand allows for relaxation of the supercoils. Once the tension caused by supercoiling has been removed, the backbone of the cut strand is religated and Top1 released. This mechanism has been substantiated by crystallography of a stable form of the Top1-DNAcc.

The dependency of living organisms on topoisomerases in processes like DNA replication during cell division has made topoisomerases attractive drug targets for anticancer chemotherapy. The search for Top1 inhibitors was eventually rewarded with the isolation of camptothecin (1) in 1966 from an extract of the Chinese tree *Camptotheca acuminata*.

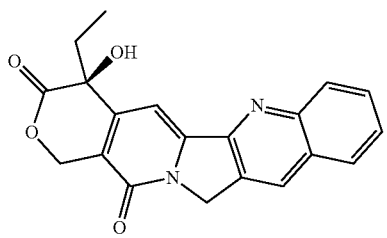

Camptothecin (1)

It was found that camptothecin was capable of inducing DNA cleavage in the presence of Top1. The ability of camptothecin to bind to and stabilize the Top1-DNAcc by forming a drug-Top1-DNA ternary complex lies at the heart of its mechanism of action. Further development of camptothecin as an anticancer drug was hindered by its poor water solubility. Screening of a number of synthetic analogues of camptothecin led to the clinically used Top1 inhibitors, topotecan and irinotecan, which possess basic functionality and thus improved water solubility and bioavailability. Unfortunately, the derivatives of camptothecin have limitations in their clinical use. The lactone form is in equilibrium with its carboxylate form at physiological pH, which has reduced bioavailability due to plasma protein binding. Additionally, the treatment with derivatives of camptothecin requires long infusion times due to quick reversibility of the Top1-DNAcc.

Crystallography of the camptothecin-Top1-DNA ternary complex revealed that camptothecin is capable of stabilizing the Top1-DNAcc by binding to it at the site of cleavage. The described binding mode showed an extended region of $\pi$-$\pi$ stacking between the polycyclic core of camptothecin and the DNA base pairs, as well as a number of polar interactions formed between camptothecin and Top1 residues. The intercalation of camptothecin into the Top1-DNAcc increases the distance between ends of the broken DNA strand and prevents religation, resulting in prolonged covalent attachment of Top1 to the DNA.

A new class of Top1 inhibitors, the indenoisoquinolines, emerged with the isolation of NSC 314622 (2) as a byproduct of nitidine chloride synthesis.

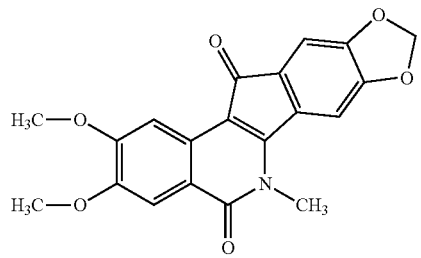

NSC 314622 (2)

A COMPARE analysis revealed similar cytotoxicity profiles between (1) and (2). However, observed differences in DNA cleavage site specificity between camptothecins and indenoisoquinolines suggested that different genes might be targeted more specifically with indenoisoquinolines. Also and in contrast to (1), the Top1-DNAcc trapped by (2) was more persistent in both cell- and enzyme-based assays. Moreover, a structural comparison of the indenoisoquinolines and the camptothecins suggested that indenoisoquinolines would likely have enhanced chemical stability relative to that of the camptothecins. Further structure optimization of (2) and biological assessment of synthesized analogues led to the discovery of a number of potent Top1 inhibitors, including MJIII-65 (3a), NSC 724998 (NSC 743400, LMP400, 3b), and NSC725776 (LMP776, 3c). The morpholinopropyl (3b) and imidazolylpropyl (3c) compounds have been promoted to phase I clinical trials at National Cancer Institute.

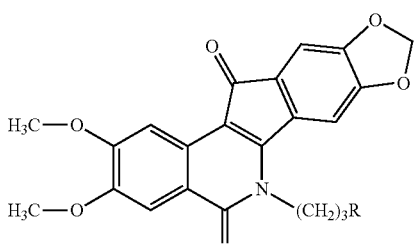

(3a) R = NH(CH$_2$)$_2$OH
(3b) R = morphlino
(3c) R = imidazolyl

It has been discovered that azaindenoisoquinolines, as described below, demonstrate improved water solubility without any decrease in Top1 inhibitory activity or cytotoxicity. Analysis of the biological results reveals that smaller lactam ring substituents enable intercalation into both free DNA and Top1-DNA cleavage complex, whereas larger substituents only allow binding to the cleavage complex but not free DNA. Free DNA binding suppresses Top1-catalyzed DNA cleavage at high drug concentrations, whereas DNA cleavage and inhibition of religation occurs at low drug concentration.

In one illustrative embodiment of the invention, a compound of the following formula:

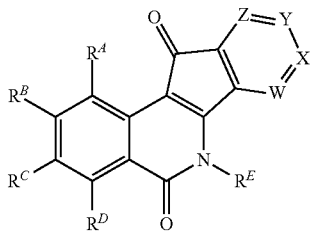

or a pharmaceutically acceptable salt thereof, wherein each of W, X, Y, Z, $R^A$, $R^B$, $R^C$, $R^D$ and $R^E$ is defined below, is described herein.

In addition, various genera and subgenera of each of W, X, Y, Z, $R^A$, $R^B$, $R^C$, $R^D$ and $R^E$ are described herein. It is to be understood that all possible combinations of the various genera and subgenera of each of W, X, Y, Z, $R^A$, $R^B$, $R^C$, $R^D$ and $R^E$ described herein represent additional illustrative embodiments of compounds of the invention described herein. It is to be further understood that each of those additional illustrative embodiments of compounds may be used in any of the compositions, methods, and/or uses described herein.

In another embodiment, pharmaceutical compositions containing one or more of the compounds are also described herein. In one aspect, the compositions include a therapeutically effective amount of the one or more compounds for treating a patient with cancer. It is to be understood that the compositions may include other component and/or ingredients, including, but not limited to, other therapeutically active compounds, and/or one or more carriers, diluents, excipients, and the like. In another embodiment, methods for using the compounds and pharmaceutical compositions for treating patients with cancer are also described herein. In one aspect, the methods include the step of administering one or more of the compounds and/or compositions described herein to a patient with cancer. In another aspect, the methods include administering a therapeutically effective amount of the one or more compounds and/or compositions described herein for treating patients with cancer.

It is appreciated herein that the compounds described herein may be used alone or in combination with other compounds useful for treating cancer, including those compounds that may be therapeutically effective by the same or different modes of action. In addition, it is appreciated herein that the compounds described herein may be used in combination with other compounds that are administered to treat other symptoms of cancer, such as compounds administered to relieve nausea, vomiting, pain, and the like.

DETAILED DESCRIPTION

Illustrative embodiments of the invention are described by the following enumerated clauses, further support is found in Appendix A herein incorporated by reference in its entirety:

1. A compound of the formula

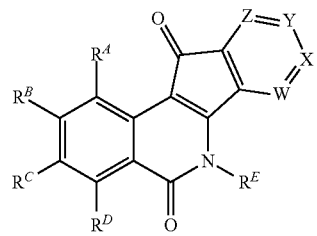

or a pharmaceutically acceptable salt thereof, wherein:

each of $R^A$, $R^B$, $R^C$ and $R^D$ is independently hydrogen, hydroxy, acyloxy, halo, cyano, nitro, optionally substituted (1-6C) alkyl or optionally substituted (1-6C) alkoxy; or two adjacent $R^A$, $R^B$, $R^C$ and $R^D$ radicals form a methylenedioxy or ethylenedioxy group and each of the others is defined as above;

$R^E$ is (1-6C) alkyl or —(CH$_2$)$_n$R$^N$;

n is 2, 3 or 4;

$R^N$ is 1-imidazolyl, 1,2,4-triazol-2-yl or azido; or $R^N$ is —NR$^1$R$^2$; in which each of R$^1$ and R$^2$ is independently hydrogen or (1-3C) alkyl or in which one of R$^1$ and R$^2$ is hydrogen or methyl and the other of R$^1$ and R$^2$ is 2-hydroxyethyl or methyl; or —NR$^1$R$^2$ forms a pyrrolidino, piperidino, piperazino, morpholino or thiomorpholino group, each of which may bear one or more methyl substituents; in which a pyrrolidino or piperidino may bear a hydroxy substituent on a carbon not bound to nitrogen; and in which a pyrrolidino or piperidino may be a 3,4-didehydro moiety;

W is N or CR$^W$; X is N or CR$^X$; Y is N or CR$^Y$; Z is N or CR$^Z$;

one of W, X, Y and Z is N, and each of the others of W, X, Y and Z is CR$^W$, CR$^X$, CR$^Y$ or CR$^Z$, respectively; and each of R$^W$, R$^X$, R$^Y$ and R$^Z$, is independently hydrogen, (1-3C) alkyl, (1-3C) alkoxy, or acyloxy.

2. The compound of any preceding clause wherein each of $R^A$ and $R^D$ is hydrogen.

3. The compound of any preceding clause wherein each of $R^B$ and $R^C$ is methoxy, or $R^B$ is hydrogen and $R^C$ is nitro.

4. The compound of any preceding clause wherein $R^E$ is —(CH$_2$)$_n$R$^N$:

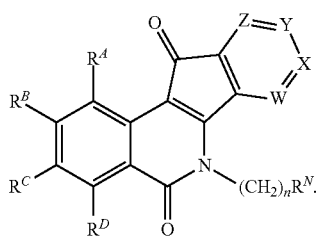

5. The compound of any preceding clause wherein n is 3 and $R^N$ is dimethylamino or morpholino.

6. The compound of any preceding clause wherein each of $R^W$, $R^X$ and $R^Z$ is hydrogen; and $R^Y$ is hydrogen or methoxy.

7. The compound of any of clauses 1-6 wherein W is N.

8. The compound of any of clauses 1-6 wherein X is N.

9. The compound of any of clauses 1-6 wherein Y is N.

10. The compound of any of clauses 1-6 wherein Z is N.

11. A pharmaceutical composition comprising a compound of any preceding clause, or a pharmaceutically acceptable salt thereof, together with a diluent, excipient or carrier.

12. A method of treatment of cancer comprising administering a therapeutically effective amount of a compound of any preceding clause, or a pharmaceutically acceptable salt thereof, to a patient in need thereof.

13. The method of clause 12 wherein the cancer is ovarian cancer, small-cell lung cancer, cervical cancer, colon cancer or rectal cancer.

14. A process for the preparation of a compound as described in clause 1, or a pharmaceutically acceptable salt thereof, comprising one or more of the steps of the group consisting of:

a. treating a homophthalic anhydride of the formula (A)

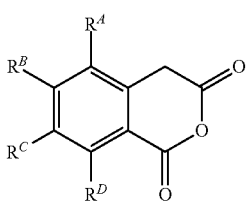

with a cyanopyridine of formula (B)

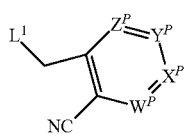

to form a compound of formula (C)

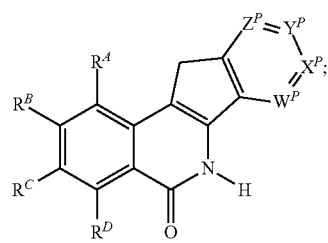

b. oxidizing a compound of formula (C), to afford a compound of formula (D)

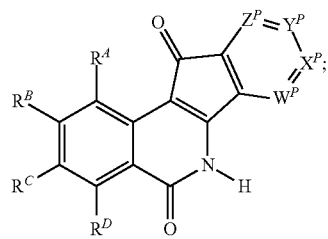

c. alkylating a compound of formula (D) with a compound of formula $R^E$-$L^2$; to afford a compound of clause 1; and d. alkylating a compound of formula H—$R^N$ with a compound of formula (E)

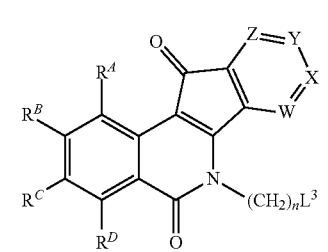

to afford a compound of clause 1; wherein
  each of n, W, X, Y, Z, $R^A$, $R^B$, $R^C$, $R^D$ and $R^N$ is defined as in clause 1;
  $W^P$ is N or $CR^{WP}$; $X^P$ is N or $CR^{XP}$; $Y^P$ is N or $CR^{YP}$; $Z^P$ is N or $CR^{ZP}$;
  one of $W^P$, $X^P$, $Y^P$ and $Z^P$ is N, and each of the others of $W^P$, $X^P$, $Y^P$ and $Z^P$ is $CR^{WP}$, $CR^{XP}$, $CR^{YP}$ or $CR^{ZP}$, respectively; and
  each $R^{WP}$, $R^{XP}$, $R^{YP}$ and $R^{ZP}$ is independently hydrogen, (1-3C) alkyl or (1-3C) alkoxy, or is a precursor or protected derivative thereof; and
  each of $L^1$, $L^2$ and $L^3$ is a leaving group.

14.1 The process of the preceding clause 14 wherein $L^1$ is chloro, bromo or iodo; and each of $L^2$ and $L^3$ is independently chloro, bromo, iodo, or a sulfonate generated from a corresponding alcohol or an oxyphosphonium residue generated from a corresponding alcohol.

14.2 The process of the preceding clause 14 wherein $L^1$ is bromo; $L^2$ is the oxytriphenylphosphonium residue generated from the corresponding alcohol; and $L^3$ is bromo.

14.3 The process of any of the preceding clauses 14-14.2 wherein a precursor of protected derivative of a hydrogen is a halo and of a (1-3C) alkoxy is a hydroxy.

15. A compound, or salt thereof, selected from the group consisting of a compound of formula (C)

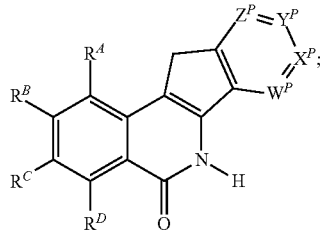

a compound of formula (D)

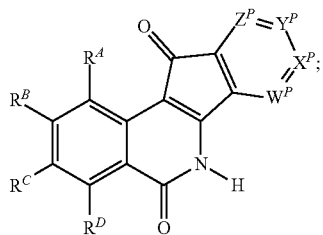

and
a compound of formula (E)

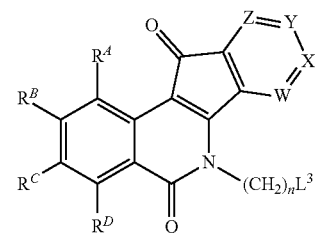

wherein
  $L^3$ is a leaving group;
  each of n, W, X, Y, Z, $R^A$, $R^B$, $R^C$ and $R^D$ is defined as in clause 1;
  $W^P$ is N or $CR^{WP}$; $X^P$ is N or $CR^{XP}$; $Y^P$ is N or $CR^{YP}$; $Z^P$ is N or $CR^{ZP}$;
  one of $W^P$, $X^P$, $Y^P$ and $Z^P$ is N, and each of the others of $W^P$, $X^P$, $Y^P$ and $Z^P$ is $CR^{WP}$, $CR^{XP}$, $CR^{YP}$ or $CR^{ZP}$, respectively; and
  each $R^{WP}$, $R^{XP}$, $R^{YP}$ and $R^{ZP}$ is independently hydrogen, (1-3C) alkyl or (1-3C) alkoxy, or is a precursor or protected derivative thereof.

15.1 The compound of the preceding clause 15 wherein $L^3$ is chloro, bromo, iodo, or a sulfonate generated from a corresponding alcohol or an oxyphosphonium residue generated from a corresponding alcohol.

15.2 The compound of the preceding clause 15 wherein $L^3$ is bromo.

15.3 The compound of any of the preceding clauses 15-15.2 wherein a precursor of protected derivative of a hydrogen is a halo and of a (1-3C) alkoxy is a hydroxy.

16. The compound of any of the preceding clauses wherein halo is chloro, bromo or iodo.

16.1. The compound of any preceding clause wherein acyloxy is a group of formula —C(O)$R^G$ or —C(O)NH$R^G$ in which $R^G$ is hydrogen; or $R^G$ is (1-18C)alkyl which may include one or more ether linkages between carbons not bonded to an oxygen or a nitrogen atom or one or more hydroxy groups on carbons not bonded to an oxygen or a nitrogen atom; or $R^G$ is (1-6C)alkyl which may bear an optionally substituted aryl, aryloxy, heteroaryl or heteroaryloxy group.

16.2 The compound of any preceding clause wherein an optionally substituted aryl (or the aryl portion of aryloxy) comprises monocyclic and polycyclic aromatic carbocyclic groups of 6 to 10 carbon atoms, each of which may be substituted with one or more substituents selected from the group consisting of amino, (1-6C)alkyl, hydroxy, (1-6C)alkoxy, halo, cyano, (1-6C)alkylcarbonyl, (1-6C)alkoxycarbonyl, carboxy, and aminocarbonyl; and an optionally substituted heteroaryl (or the heteroaryl portion of heteroaryloxy) comprises monocyclic and polycyclic heteroaromatic groups of 5 to 10 ring atoms consisting of carbon and one to four heteroatoms selected from the group consisting of oxygen, sulfur and nitrogen, in which a carbon may be substituted with one or more substituents selected from the group consisting of amino, (1-6C)alkyl, hydroxy, (1-6C)alkoxy, halo, cyano, (1-6C)alkylcarbonyl, (1-6C)alkoxycarbonyl, carboxy, and aminocarbonyl; and a nitrogen may be substituted with (1-6C)alkyl.

16.3 The pharmaceutically acceptable salt of any preceding clause wherein the salt is the acid addition salt of an acid providing a pharmaceutically acceptable anion.

In each of the descriptions and structural formulae herein, it is to be understood that, unless specified to the contrary, all tautomers are included. Thus, for example, a "pyridone-type" structure may be represented by a "hydroxy-pyridine," as well. As used herein, alkyl, alkoxy, etc. denote both straight and branched groups; but reference to an individual radical such as "propyl" embraces only the straight chain ("normal") radical, a branched chain isomer such as "isopropyl" being specifically denoted.

Further, in each of the foregoing and following embodiments, it is to be understood that the formulae include and represent not only all pharmaceutically acceptable salts of the compounds, but also include any and all hydrates and/or solvates of the compound formulae or salts thereof. It is to be appreciated that certain functional groups, such as the hydroxy, amino, and like groups form complexes and/or coordination compounds with water and/or various solvents, in the various physical forms of the compounds. Accordingly, the above formulae are to be understood to include and represent those various hydrates and/or solvates. In each of the foregoing and following embodiments, it is also to be understood that the formulae include and represent each possible isomer, such as stereoisomers and geometric isomers, both individually and in any and all possible mixtures. In each of the foregoing and following embodiments, it is also to be understood that the formulae include and represent any and all crystalline forms, partially crystalline forms, and non crystalline and/or amorphous forms of the compounds.

The compounds described herein may contain one or more chiral centers, or may otherwise be capable of existing as multiple stereoisomers. It is to be understood that in one embodiment, the invention described herein is not limited to any particular sterochemical requirement, and that the compounds, and compositions, methods, uses, and medicaments that include them may be optically pure, or may be any of a variety of stereoisomeric mixtures, including racemic and other mixtures of enantiomers, other mixtures of diastereomers, and the like. It is also to be understood that such mixtures of stereoisomers may include a single stereochemical configuration at one or more chiral centers, while including mixtures of stereochemical configuration at one or more other chiral centers.

Similarly, the compounds described herein may be include geometric centers, such as cis, trans, E, and Z double bonds. It is to be understood that in another embodiment, the invention described herein is not limited to any particular geometric isomer requirement, and that the compounds, and compositions, methods, uses, and medicaments that include them may be pure, or may be any of a variety of geometric isomer mixtures. It is also to be understood that such mixtures of geometric isomers may include a single configuration at one or more double bonds, while including mixtures of geometry at one or more other double bonds.

As used herein, the term "aryl" includes monocyclic and polycyclic aromatic carbocyclic groups, each of which may be optionally substituted. Illustrative aromatic carbocyclic groups described herein include, but are not limited to, phenyl, naphthyl, and the like. As used herein, the term "heteroaryl" includes aromatic heterocyclic groups, each of which may be optionally substituted. Illustrative aromatic heterocyclic groups include, but are not limited to, pyridinyl, pyrimidinyl, pyrazinyl, triazinyl, tetrazinyl, quinolinyl, quinazolinyl, quinoxalinyl, thienyl, pyrazolyl, imidazolyl, oxazolyl, thiazolyl, isoxazolyl, isothiazolyl, oxadiazolyl, thiadiazolyl, triazolyl, benzimidazolyl, benzoxazolyl, benzthiazolyl, benzisoxazolyl, benzisothiazolyl, and the like.

As used herein, the term "amino" includes the group $NH_2$, alkylamino, and dialkylamino, where the two alkyl groups in dialkylamino may be the same or different, i.e. alkylalkylamino. Illustratively, amino includes methylamino, ethylamino, dimethylamino, methylethylamino, and the like.

If not commercially available, a necessary starting material for the preparation of a compound of the formula described herein may be prepared by a novel process described herein or one analogous thereto or by a procedure which is selected from standard techniques of organic chemistry, including aromatic substitution and transformation, from techniques which are analogous to the syntheses of known, structurally similar compounds, and techniques which are analogous to the above described procedures or procedures described in the Examples. It will be clear to one skilled in the art that a variety of sequences is available for the preparation of the starting materials. A novel intermediate or starting material compound provides a further aspect of the invention.

The term "administering" as used herein includes all means of introducing the compounds and compositions described herein to the patient, including, but are not limited to, oral (po), intravenous (iv), intramuscular (im), subcutaneous (sc), transdermal, inhalation, buccal, ocular, sublingual, vaginal, rectal, and the like. The compounds and compositions described herein may be administered in unit dosage forms and/or formulations containing conventional nontoxic pharmaceutically-acceptable carriers, adjuvants, and vehicles.

Illustrative formats for oral administration include tablets, capsules, elixirs, syrups, and the like.

Illustrative routes for parenteral administration include intravenous, intraarterial, intraperitoneal, epidural, intraurethral, intrasternal, intramuscular and subcutaneous, as well as any other art recognized route of parenteral administration.

Illustrative means of parenteral administration include needle (including microneedle) injectors, needle-free injectors and infusion techniques, as well as any other means of parenteral administration recognized in the art. Parenteral formulations are typically aqueous solutions which may contain excipients such as salts, carbohydrates and buffering agents (preferably at a pH in the range from about 3 to about 9), but, for some applications, they may be more suitably formulated as a sterile non-aqueous solution or as a dried form to be used in conjunction with a suitable vehicle such as sterile, pyrogen-free water. The preparation of parenteral formulations under sterile conditions, for example, by lyophilization, may readily be accomplished using standard pharmaceutical techniques well known to those skilled in the art. Parenteral administration of a compound is illustratively performed in the form of saline solutions or with the compound incorporated into liposomes. In cases where the compound in itself is not sufficiently soluble to be dissolved, a solubilizer such as ethanol can be applied.

The dosage of each compound of the claimed combinations depends on several factors, including: the administration method, the condition to be treated, the severity of the condition, whether the condition is to be treated or prevented, and the age, weight, and health of the person to be treated. Additionally, pharmacogenomic (the effect of genotype on the pharmacokinetic, pharmacodynamic or efficacy profile of a therapeutic) information about a particular patient may affect the dosage used.

It is to be understood that in the methods described herein, the individual components of a co-administration, or combination can be administered by any suitable means, contemporaneously, simultaneously, sequentially, separately or in a single pharmaceutical formulation. Where the co-administered compounds or compositions are administered in separate dosage forms, the number of dosages administered per day for each compound may be the same or different. The compounds or compositions may be administered via the same or different routes of administration. The compounds or compositions may be administered according to simultaneous or alternating regimens, at the same or different times during the course of the therapy, concurrently in divided or single forms.

Illustratively, administering includes local use, such as when administered locally to the site of disease, injury, or defect, or to a particular organ or tissue system. Illustrative local administration may be performed during open surgery, or other procedures when the site of disease, injury, or defect is accessible. Alternatively, local administration may be performed using parenteral delivery where the compound or compositions described herein are deposited locally to the site without general distribution to multiple other non-target sites in the patient being treated. It is further appreciated that local administration may be directly in the injury site, or locally in the surrounding tissue. Similar variations regarding local delivery to particular tissue types, such as organs, and the like, are also described herein. Illustratively, compounds may be administered directly to the nervous system including, but not limited to, intracerebral, intraventricular, intracerebroventricular, intrathecal, intracisternal, intraspinal and/or peri-spinal routes of administration by delivery via intracranial or intravertebral needles and/or catheters with or without pump devices.

The term "therapeutically effective amount" as used herein, refers to that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. In one aspect, the therapeutically effective amount is that which may treat or alleviate the disease or symptoms of the disease at a reasonable benefit/ risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the disorder being treated and the severity of the disorder; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician of ordinary skill.

Depending upon the route of administration, a wide range of permissible dosages are contemplated herein, including doses falling in the range from about 1 µg/kg to about 1 g/kg. The dosages may be single or divided, and may administered according to a wide variety of protocols, including q.d., b.i.d., t.i.d., or even every other day, once a week, once a month, once a quarter, and the like. In each of these cases it is understood that the therapeutically effective amounts described herein correspond to the instance of administration, or alternatively to the total daily, weekly, month, or quarterly dose, as determined by the dosing protocol.

When given systemically, such as parenterally, illustrative doses include those in the range from about 0.01 mg/kg to about 100 mg/kg, or about 0.01 mg/kg to about 10 mg/kg, or about 0.1 mg/kg to about 100 mg/kg, or about 0.1 mg/kg to about 10 mg/kg.

When given systemically, such as orally, illustrative doses include those in the range from about 0.1 mg/kg to about 1000 mg/kg, or about 0.1 mg/kg to about 100 mg/kg, or about 0.1 mg/kg to about 10 mg/kg, or about 1 mg/kg to about 1000 mg/kg, or about 1 mg/kg to about 100 mg/kg, or about 1 mg/kg to about 10 mg/kg.

In addition to the illustrative dosages and dosing protocols described herein, it is to be understood that an effective amount of any one or a mixture of the compounds described herein can be readily determined by the attending diagnostician or physician by the use of known techniques and/or by observing results obtained under analogous circumstances. In determining the effective amount or dose, a number of factors are considered by the attending diagnostician or physician, including, but not limited to the species of mammal, including human, its size, age, and general health, the specific disease or disorder involved, the degree of or involvement or the severity of the disease or disorder, the response of the individual patient, the particular compound administered, the mode of administration, the bioavailability characteristics of the preparation administered, the dose regimen selected, the use of concomitant medication, and other relevant circumstances.

In making the pharmaceutical compositions of the compounds described herein, a therapeutically effective amount of one or more compounds in any of the various forms described herein may be mixed with one or more excipients, diluted by one or more excipients, or enclosed within such a carrier which can be in the form of a capsule, sachet, paper, or other container. Excipients may serve as a diluent, and can be solid, semi-solid, or liquid materials, which act as a vehicle, carrier or medium for the active ingredient. Thus, the formulation compositions can be in the form of tablets, pills, powders, lozenges, sachets, cachets, elixirs, suspensions, emulsions, solutions, syrups, aerosols (as a solid or in a liquid medium), ointments, soft and hard gelatin capsules, suppositories, sterile injectable solutions, and sterile packaged powders. The compositions may contain anywhere from about 0.1% to about 99.9% active ingredients, depending upon the selected dose and dosage form.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions can be formulated so as to provide quick, sustained or delayed release of the active ingredient after administration to the patient by employing procedures known in the art. It is to be understood that one or more carriers, one or more diluents, one or more excipients, and combinations of the foregoing may be used in making the pharmaceutical compositions described herein. It is appreciated that the carriers, diluents, and excipients used to prepare the compositions described herein are advantageously GRAS (generally regarded as safe) compounds.

Examples of emulsifying agents are naturally occurring gums (e.g., gum acacia or gum tragacanth) and naturally occurring phosphatides (e.g., soybean lecithin and sorbitan monooleate derivatives). Examples of antioxidants are butylated hydroxy anisole (BHA), ascorbic acid and derivatives thereof, tocopherol and derivatives thereof, butylated hydroxy anisole, and cysteine. Examples of preservatives are parabens, such as methyl or propyl p-hydroxybenzoate, and benzalkonium chloride. Examples of humectants are glycerin, propylene glycol, sorbitol, and urea. Examples of penetration enhancers are propylene glycol, DMSO, triethanolamine, N,N-dimethylacetamide, N,N-dimethylformamide, 2-pyrrolidone and derivatives thereof, tetrahydrofurfuryl alcohol, and AZONE. Examples of chelating agents are sodium EDTA, citric acid, and phosphoric acid. Examples of gel forming agents are CARBOPOL, cellulose derivatives, bentonite, alginates, gelatin and polyvinylpyrrolidone. Examples of ointment bases are beeswax, paraffin, cetyl palmitate, vegetable oils, sorbitan esters of fatty acids (Span), polyethylene glycols, and condensation products between sorbitan esters of fatty acids and ethylene oxide (e.g., polyoxyethylene sorbitan monooleate (TWEEN)).

Solid Dosage Forms for Oral Use. Formulations for oral use include tablets containing the active ingredient(s) in a mixture with non-toxic pharmaceutically acceptable excipients. These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the active drug substance in a predetermined pattern (e.g., in order to achieve a controlled release formulation) or it may be adapted not to release the active drug substance until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). Furthermore, a time delay material such as, e.g., glyceryl monostearate or glyceryl distearate may be employed.

The solid tablet compositions may include a coating adapted to protect the composition from unwanted chemical changes, (e.g., chemical degradation prior to the release of the active drug substance). The coating may be applied on the solid dosage form in a similar manner as that described in Encyclopedia of Pharmaceutical Technology.

Controlled Release Oral Dosage Forms. Controlled release compositions for oral use may, e.g., be constructed to release the active drug by controlling the dissolution and/or the diffusion of the active drug substance. Illustrative sustained release formulations are described in U.S. Pat. Nos. 3,847,770; 3,916,899; 3,536,809; 3,598,123; 3,630,200; 4,008,719; 4,687,610; 4,769,027; 5,674,533; 5,059,595; 5,591,767; 5,120,548; 5,073,543; 5,639,476; 5,354,566; and 5,733,566, the disclosures of which are incorporated herein by reference.

Dissolution or diffusion controlled release can be achieved by appropriate coating of a tablet, capsule, pellet, or granulate formulation of compounds, or by incorporating the compound into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

A controlled release composition containing one or more of the compounds of the claimed combinations may also be in the form of a buoyant tablet or capsule (i.e., a tablet or capsule that, upon oral administration, floats on top of the gastric content for a certain period of time). A buoyant tablet formulation of the compound(s) can be prepared by granulating a mixture of the drug(s) with excipients and 20-75% w/w of hydrocolloids, such as hydroxyethylcellulose, hydroxypropylcellulose, or hydroxypropylmethylcellulose. The obtained granules can then be compressed into tablets. On contact with the gastric juice, the tablet forms a substantially water-impermeable gel barrier around its surface. This gel barrier takes part in maintaining a density of less than one, thereby allowing the tablet to remain buoyant in the gastric juice.

Liquids for Oral Administration. Powders, dispersible powders, or granules suitable for preparation of an aqueous suspension by addition of water are convenient dosage forms for oral administration. Formulation as a suspension provides the active ingredient in a mixture with a dispersing or wetting agent, suspending agent, and one or more preservatives. Suitable dispersing or wetting agents are, for example, naturally-occurring phosphatides (e.g., lecithin or condensation products of ethylene oxide with a fatty acid, a long chain aliphatic alcohol, or a partial ester derived from fatty acids) and a hexitol or a hexitol anhydride (e.g., polyoxyethylene stearate, polyoxyethylene sorbitol monooleate, polyoxyethylene sorbitan monooleate, and the like). Suitable suspending agents are, for example, sodium carboxymethylcellulose, methylcellulose, sodium alginate, and the like.

Parenteral Compositions. The pharmaceutical composition may also be administered parenterally by injection, infusion or implantation (intravenous, intramuscular, subcutaneous, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation. Formulations can be found in Remington: The Science and Practice of Pharmacy, supra.

Compositions for parenteral use may be provided in unit dosage forms (e.g., in single-dose ampoules), or in vials containing several doses and in which a suitable preservative may be added (see below). The composition may be in form of a solution, a suspension, an emulsion, an infusion device, or a delivery device for implantation, or it may be presented as a dry powder to be reconstituted with water or another suitable vehicle before use. Apart from the active drug(s), the composition may include suitable parenterally acceptable carriers and/or excipients. The active drug(s) may be incorporated into microspheres, microcapsules, nanoparticles, liposomes, or the like for controlled release. Furthermore, the composition may include suspending, solubilizing, stabilizing, pH-adjusting agents, and/or dispersing agents.

As indicated above, the pharmaceutical compositions described herein may be in the form suitable for sterile injection. To prepare such a composition, the suitable active drug(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution. The aqueous formulation may also contain one or more preservatives (e.g., methyl, ethyl or n-propyl p-hydroxybenzoate). In cases where one of the compounds is only sparingly or slightly soluble in water, a dissolution enhancing or solubilizing agent can be added, or the solvent may include 10-60% w/w of propylene glycol or the like.

Controlled Release Parenteral Compositions. Controlled release parenteral compositions may be in form of aqueous suspensions, microspheres, microcapsules, magnetic microspheres, oil solutions, oil suspensions, or emulsions. Alternatively, the active drug(s) may be incorporated in biocompatible carriers, liposomes, nanoparticles, implants, or infusion devices. Materials for use in the preparation of microspheres and/or microcapsules are, e.g., biodegradable/bioerodible polymers such as polygalactin, poly-(isobutyl cyanoacrylate), poly(2-hydroxyethyl-L-glutamine) and, poly(lactic acid). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(lactic acid), poly(glycolic acid) or poly(ortho esters)).

Intraocular and/or Periocular Compositions: The pharmaceutical composition can also be included in any suitable pharmaceutical preparation or system for administration via intraocular or periocular routes of administration, together with pharmaceutically acceptable carriers, adjuvants or vehicles. Targeting of ocular tissues may be accomplished in any one of a variety of ways. The pharmaceutical preparation for intraocular or periocular administration may also include one or more excipient components, such as effective amounts of buffering agents, preservatives, emulsifiers, salts, lubricants, polymers, solvents, and other known excipients for ocular pharmaceutical formulations, and the like. In one embodiment, the pharmaceutical composition includes an emulsifier and a buffered carrier such as Polysorbate 80 in HBSS (Hanks Balanced Salt Solution).

The pharmaceutical preparation can be administered by any route of ocular administration known in the art including, but not limited to, topical ocular, subtenons, subconjunctival, intracameral, or intravitreal routes. In one embodiment, the pharmaceutical preparation can be delivered topically, e.g., via an eye drop, gel, ointment, or salve. In other embodiments, the pharmaceutical preparation can be delivered via an acute delivery system, e.g., using nanotubes, local injection, micro-injection, syringe or scleral deposition, or ultrasound.

Suitable water soluble buffering agents include, without limitation, alkali and alkaline earth carbonates, phosphates, bicarbonates, citrates, borates, acetates, succinates and the like, such as sodium phosphate, citrate, borate, acetate, bicarbonate, carbonate and the like. These agents are advantageously present in amounts sufficient to maintain a pH of the system of between about 2 to about 9, and more preferably about 4 to about 8. As such the buffering agent may be as much as about 5% by weight of the total system.

Suitable water soluble preservatives include sodium bisulfite, sodium bisulfate, sodium thiosulfate, ascorbate, benzalkonium chloride, chlorobutanol, thimerosal, phenylmercuric acetate, phenylmercuric borate, phenylmercuric nitrate, parabens, methylparaben, polyvinyl alcohol, benzyl alcohol, phenylethanol and the like and mixtures thereof. Such agents may be present in amounts as needed, such as from about 0.001 to about 5% by weight, or from about 0.01 to about 2% by weight.

Intraocular Compositions for injection are described herein and include injection into the aqueous or vitreous humor of the eye. In one embodiment, the compounds and/or compositions described herein are administered via intraocular sustained delivery (such using VITRASERT or ENVISION, or related technologies). In another embodiment, the compounds and/or compositions are delivered by posterior suborbital injection.

Compositions for Inhalation. For administration by inhalation, typical dosage forms include nasal sprays and aerosols. In a typically nasal formulation, the active ingredient(s) are dissolved or dispersed in a suitable vehicle. The pharmaceutically acceptable vehicles and excipients (as well as other pharmaceutically acceptable materials present in the composition such as diluents, enhancers, flavoring agents, and preservatives) are selected in accordance with conventional pharmaceutical practice in a manner understood by the persons skilled in the art of formulating pharmaceuticals.

Percutaneous and Topical Compositions. The pharmaceutical compositions may also be administered topically on the skin for percutaneous absorption in dosage forms or formulations containing conventionally non-toxic pharmaceutical acceptable carriers and excipients including microspheres and liposomes. The formulations include creams, ointments, lotions, liniments, gels, hydrogels, solutions, suspensions, sticks, sprays, pastes, plasters, and other kinds of transdermal drug delivery systems. The pharmaceutically acceptable carriers or excipients may include emulsifying agents, antioxidants, buffering agents, preservatives, humectants, penetration enhancers, chelating agents, gel-forming agents, ointment bases, perfumes, and skin protective agents.

The pharmaceutical compositions described above for topical administration on the skin may also be used in connection with topical administration onto or close to the part of the body that is to be treated. The compositions may be adapted for direct application or for introduction into relevant orifice(s) of the body (e.g., rectal, urethral, vaginal or oral orifices). The composition may be applied by means of special drug delivery devices such as dressings or alternatively plasters, pads, sponges, strips, or other forms of suitable flexible material.

Controlled Release Percutaneous and Topical Compositions. There are several approaches for providing rate control over the release and transdermal permeation of a drug, including: membrane-moderated systems, adhesive diffusion-controlled systems, matrix dispersion-type systems, and microreservoir systems. A controlled release percutaneous and/or topical composition may be obtained by using a suitable mixture of the above-mentioned approaches.

In a membrane-moderated system, the active drug is present in a reservoir which is totally encapsulated in a shallow compartment molded from a drug-impermeable laminate, such as a metallic plastic laminate, and a rate-controlling polymeric membrane such as a microporous or a nonporous polymeric membrane (e.g., ethylene-vinyl acetate copolymer). The active compound is only released through the rate-controlling polymeric membrane. In the drug reservoir, the active drug substance may either be dispersed in a solid polymer matrix or suspended in a viscous liquid medium such as silicone fluid. On the external surface of the polymeric membrane, a thin layer of an adhesive polymer is applied to achieve an intimate contact of the transdermal system with the skin surface. The adhesive polymer is preferably a hypoallergenic polymer that is compatible with the active drug.

In an adhesive diffusion-controlled system, a reservoir of the active drug is formed by directly dispersing the active drug in an adhesive polymer and then spreading the adhesive containing the active drug onto a flat sheet of substantially drug-impermeable metallic plastic backing to form a thin drug reservoir layer. A matrix dispersion-type system is characterized in that a reservoir of the active drug substance is formed by substantially homogeneously dispersing the active drug substance in a hydrophilic or lipophilic polymer matrix and then molding the drug-containing polymer into a disc with a substantially well-defined surface area and thickness. The adhesive polymer is spread along the circumference to form a strip of adhesive around the disc.

In a microreservoir system, the reservoir of the active substance is formed by first suspending the drug solids in an aqueous solution of water-soluble polymer, and then dispersing the drug suspension in a lipophilic polymer to form a plurality of microscopic spheres of drug reservoirs.

Rectal Compositions. For rectal application, suitable dosage forms for a composition include suppositories (emulsion or suspension type), and rectal gelatin capsules (solutions or suspensions). In a typical suppository formulation, the active drug(s) are combined with an appropriate pharmaceutically acceptable suppository base such as cocoa butter, esterified fatty acids, glycerinated gelatin, and various water-soluble or dispersible bases like polyethylene glycols and polyoxyethylene sorbitan fatty acid esters. Various additives, enhancers, or surfactants may be incorporated.

The following examples further illustrate specific embodiments of the invention; however, the following illustrative examples should not be interpreted in any way to limit the invention.

EXAMPLES

General

Melting points were determined using capillary tubes with a Mel-Temp apparatus and are uncorrected. The nuclear magnetic resonance spectra ($^1$H and $^{13}$CNMR) were recorded using ARX300 300 MHz and DRX500 500 MHz Bruker NMR spectrometers. IR spectra were recorded using a Perkin-Elmer 1600 series FTIR spectrometer. Purity of all tested compounds was ≥95%, as established by combustion analysis. Combustion microanalyses were performed at the Purdue University Microanalysis Laboratory or Galbraith Laboratories Inc., and the reported values were within 0.4% of the calculated values. HPLC analyses were performed on a Waters 1525 binary HPLC pump/Waters 2487 dual λ absorbance detector system. Analytical thin-layer chromatography was carried out on Baker-flex silica gel IB2-F plates, and compounds were visualized with short wavelength UV light. Silica gel flash chromatography was performed using 230-400 mesh silica gel.

Abbreviations used herein include the following: AIBN, azobisisobutyronitrile; DIAD, diisopropyl azodicarboxylate; DMF, dimethylformamide; DMSO-d$_6$, dimethyl-d$_6$ sulfoxide; NBS, N-bromosuccinimide; THF, tetrahydrofuran; Top1, topoisomerase type I; Top1-DNAcc, topoisomerase type I_DNA cleavage complex; Ph, phenyl.

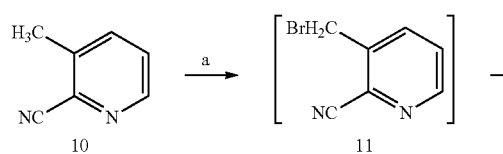

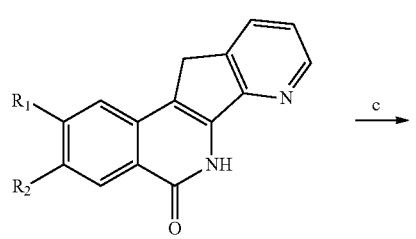

12 R$_1$ = R$_2$ = H
13 R$_1$ = R$_2$ = OCH$_3$
14 R$_1$ = H; R$_2$ = NO$_2$

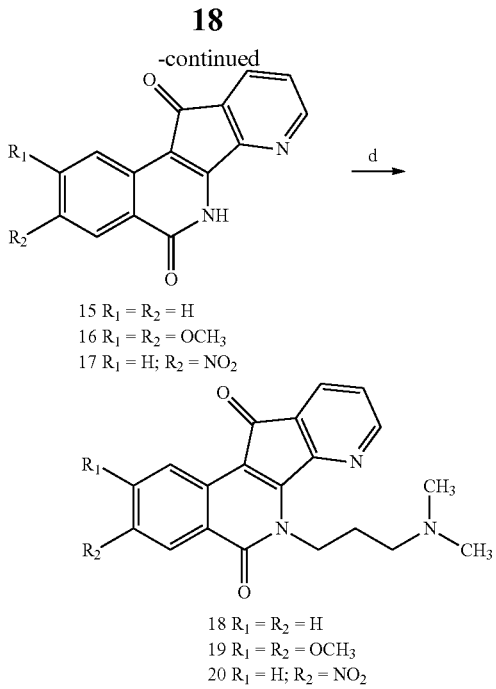

15 R$_1$ = R$_2$ = H
16 R$_1$ = R$_2$ = OCH$_3$
17 R$_1$ = H; R$_2$ = NO$_2$

18 R$_1$ = R$_2$ = H
19 R$_1$ = R$_2$ = OCH$_3$
20 R$_1$ = H; R$_2$ = NO$_2$ $^a$Reagents and conditions: (a) NBS, AIBN, 1,2-dichloroethane, reflux, 2 h; (b) 5 (for 12), 6 (for 13) or 7 (for 14), triethylamine, acetonitrile, reflux 10 h (12 31%, 13 39%, 14 12%); (c) selenium dioxide, 1,4-dioxane, reflux 16 h (15 89%, 16 26%, 14 59%); (d) DIAD, triphenylphosphine, 3-dimethylamino-1-propanol, THF, 23° C., 3 d (18 59%, 19 76%, 20 62%).

General Procedure for the Preparation of 7-Aza-5,6-dihydro-5-oxo-11H-indenol[1,2-c]isoquinolines 12-14

3-Methylpicolonitrile (10, 3.0-4.0 g, 25.4-33.9 mmol, 1 equiv), NBS (6.78-9.04 g, 38.1-50.8 mmol, 1.5 equiv), and AIBN (0.42-0.56 g, 2.5-3.4 mmol, 0.1 equiv) were diluted with 1,2-dichloroethane (80-100 mL), and the reaction mixture was heated at reflux for 2 h. The reaction mixture was concentrated to half its original volume, filtered, and the filtrate was concentrated to dryness to provide crude 11. Compound 11 was diluted with acetonitrile (100-125 mL). The appropriate homophthalic anhydride (5, 6, or 7, 6.8-12.4 g, 41.9-55.9 mmol, 1.65 equiv) was added, followed by triethylamine (18-24 mL, 127.0-169.5 mmol, 5 equiv), and the solution was heated at reflux for 10 h. The solution was allowed to cool to room temperature, and the precipitate was filtered and washed with hot acetonitrile (2×35 mL) to provide the described compound.

7-Aza-5,6-dihydro-5-oxo-11H-indeno[1,2-c]isoquinoline (12)

The general procedure provided the described compound as a gray solid (2.49 g, 31%): mp 267-269° C. IR (KBr) 3098, 1665, 1573, 1478, 767, and 756 cm$^{-1}$; $^1$HNMR (DMSO-d$_6$) δ 12.18 (s, 1H), 8.56 (dd, J=4.9 and 1.3 Hz, 1H), 8.30 (d, J=8.0 Hz, 1H), 8.02 (dd, J=7.5 and 1.1 Hz, 1H), 7.82-7.80 (m, 2H), 7.57-7.51 (m, 1H), 7.36 (dd, J=7.5 and 5.0 Hz, 1H), 3.94 (s, 2H); ESIMS m/z (rel intensity) 235 (MH$^+$, 100). Anal. Calcd for C$_{15}$H$_{10}$N$_2$O: C, 76.91; H, 4.30; N, 11.96. Found: C, 76.58; H, 4.16; N, 11.80.

7-Aza-5,6-dihydro-2,3-dimethoxy-5-oxo-11H-indeno[1,2-c]isoquinoline (13)

The general procedure provided the described compound as a purple solid (3.87 g, 39%): mp 284-286° C. I R (KBr)

3399, 3276, 1635, 1604, 1479, 1215, and 803 cm$^{-1}$; $^1$H NMR (DMSO-d$_6$) δ 11.99 (s, 1H), 8.52 (dd, J=4.9 and 1.1 Hz, 1H), 7.95 (d, J=6.9 Hz, 1H), 7.67 (s, 1H), 7.32 (dd, J=7.5 and J=4.9, 1H), 7.24 (s, 1H), 3.97 (s, 3H), 3.91 (s, 2H), 3.89 (s, 3H); ESIMS m/z (rel intensity) 295 (MH$^+$, 100).

7-Aza-5,6-dihydro-3-nitro-5-oxo-11H-indeno[1,2-c]isoquinoline (14)

The general procedure provided the desired compound as a green solid (878 mg, 12%): mp 323° C.
IR (KBr) 3096, 1691, 1607, 1508, 1330, and 834 cm$^{-1}$; $^1$H NMR (DMSO-d$_6$, 500 MHz) δ 12.74 (s, 1H), 8.95 (d, J=2.3 Hz, 1H), 8.60 (d, J=4.9 Hz, 1H), 8.52 (d, J=2.3 Hz, 1H), 8.51 (d, J=2.6 Hz, 1H), 8.06 (d, J=8.0 Hz, 1H), 8.00 (d, J=8.0 Hz, 1H), 7.41 (dd, J=7.6 and 4.9 Hz, 1H), 3.97 (s, 3H), 3.91 (s, 2H), 3.89 (s, 3H); negative ion ESIMS m/z (rel intensity) 278 [(M-H$^+$)$^-$, 100].

General Procedure for the Preparation of 7-Aza-5,6-dihydro-5,11-dioxo-11H-indeno[1,2-c]isoquinolines 15-17

The appropriate 7-aza-5,6-dihydro-5-oxo-11H-indeno-[1,2-c]isoquinoline (12-14, 0.50-1.0 g, 1.8-4.27 mmol, 1 equiv) and SeO$_2$ (0.4-0.95 g, 3.6-8.54 mmol, 2 equiv) were diluted with 1,4-dioxane (125-250 mL) and heated at reflux for 16 h. The reaction mixture was filtered, the filtrate was concentrated, and the precipitate was washed with MeOH (2-50 mL) to provide the desired product.

7-Aza-5,6-dihydro-5,11-dioxo-11H-indeno[1,2-c]isoquinoline (15)

The general procedure provided the described compound as a red-orange solid (0.94 g, 89%): mp 337° C. (dec). IR (KBr) 2979, 1678, 1575, 1085, and 770 cm$^{-1}$; $^1$H NMR (DMSO-d$_6$) δ 13.12 (s, 1H), 8.61 (dd, J=6.2 and 1.4 Hz, 1H), 8.44 (d, J=7.9 Hz, 1H), 8.23 (d, J=7.3 Hz, 1H), 7.89-7.81 (m, 2H), 7.58-7.53 (m, 1H), 7.46 (dd, J=7.3 and 5.2 Hz, 1H); negative ion ESIMS m/z (rel intensity) 247 [(M-H$^+$)$^-$, 100].

7-Aza-5,6-dihydro-2,3-dimethoxy-5,11-dioxo-11H-indeno[1,2-c]isoquinoline (16)

The general procedure provided the described compound as a dark red solid (272 mg, 26%): mp 358-359° C. IR (KBr) 3129, 2988, 1676, 1504, 1277, and 777 cm$^{-1}$; $^1$H NMR (DMSO-d$_6$) δ 12.96 (s, 1H), 8.56 (dd, J=6.2 and 1.4 Hz, 1H), 7.86-7.81 (m, 2H), 7.59 (s, 1H), 7.40 (t, J=6.8 Hz, 1H); negative ion ESIMS m/z (rel intensity) 307 [(M-H$^+$)$^-$, 100].

7-Aza-5,6-dihydro-3-nitro-5,11-dioxo-11H-indenol[1,2-c]isoquinoline (17)

The general procedure provided the described compound as a red-orange solid (310 mg, 59%): mp 351-353° C. IR (KBr) 3187, 1692, 1567, 1335, and 785 cm$^{-1}$; $^1$H NMR (DMSO-d$_6$) δ 13.75 (s, 1H), 8.86 (s, 1H), 8.69 (dd, J=5.2 and 1.3 Hz, 1H), 8.55 (s, 2H), 7.97 (dd, J=7.4 and 1.3 Hz, 1H), 7.53 (dd, J=7.4 and 5.2 Hz 1H); negative ion ESIMS m/z (rel intensity) 292 [(M-H$^+$)$^-$, 100].

General Procedure for the Preparation of 7-Azaindenoisoquinolines 18-23

The appropriate 7-aza-5,6-dihydro-5,11-dioxo-11H-indeno[1,2-c]isoquinoline (15-17, 94-248 mg, 0.31-1.0 mmol, 1 equiv) and triphenylphosphine (262-786 mg, 1.0-3.0 mmol, 3 equiv) were diluted in THF (16-50 mL). The appropriate alcohol [3-dimethylamino-1-propanol (0.17-0.21 mL, 1.46-1.82 mmol, 3 equiv) or 3-morpholinopropan-1-ol (145-435 mg, 1.0-3.0 mmol, 3 equiv)] was added, followed by DIAD (202-606 mg, 1.0-3.0 mmol, 3 equiv). The solution was stirred at room temperature for 64 h. As the reaction reached completion, all of the solid material dissolved. The reaction mixture was concentrated to dryness. The solid was purified by flash column chromatography (SiO$_2$), eluting with 1% MeOH in CHCl$_3$, to provide a dark-orange solid. The solid was further purified by treating it with 3 M HCl in methanol (15 mL) for 2 h at room temperature with stiffing. The solution was concentrated to dryness. The orange solid was diluted in ethyl ether (50 mL). The hydrochloride salt of the product precipitated and was collected using vacuum filtration, washing with ethyl ether (3-15 mL), to provide an orange solid.

7-Aza-5,6-dihydro-6-(3-dimethylaminopropyl)-5,11-dioxo-11H-indeno[1,2-c]-isoquinoline Hydrochloride (18)

The general procedure provided the described compound as an orange solid (160 mg, 59%): mp 268-270° C. IR (KBr) 3446, 1703, 1670, 1505, and 770 cm$^{-1}$; $^1$H NMR (DMSO-d$_6$) δ 10.05 (s, 1H), 8.66 (dd, J=1.5 and 5.2 Hz, 1H), 8.56 (d, J=7.8 Hz, 1H), 8.27 (d, J=7.5 Hz, 1H), 7.95 (dd, J=1.5 Hz and 7.4 Hz 1H), 7.90-7.84 (m, 1H), 7.63-7.58 (m, 1H), 7.50 (dd, J=5.2 and 7.3 Hz, 1H), 4.92 (t, J=6.8 Hz, 2H), 3.23 (p, J=5.3 and 10.1 Hz, 2H), 2.75 (s, 3H), 2.74 (s, 3H), 2.22-2.17 (m, 2H); positive ion ESIMS m/z (rel intensity) 333 [(MH$^+$), 100]. Anal. Calcd for C$_{20}$H$_{19}$N$_3$O$_2$.HCl.1.5H$_2$O: C, 60.53; H, 5.84; N, 10.59. Found: C, 60.36; H, 5.62; N, 10.45.

7-Aza-5,6-dihydro-6-(3-dimethylaminopropyl)-2,3-dimethoxy-5,11-dioxo-11H-indeno[1,2-c]isoquinoline Hydrochloride (19)

The general procedure provided the described compound as a light-orange solid (158 mg, 76%): mp 278-281° C. (dec). IR (KBr) 3407, 2456, 1702, 1654, 1476, and 779 cm$^{-1}$; $^1$H NMR (DMSO-d$_6$) δ 9.99 (s, 1H), 8.59 (dd, J=1.2 and 5.2 Hz, 1H), 7.88 (s, 1H), 7.85 (d, J=7.3 Hz, 1H), 7.54 (s, 1H), 7.43 (dd, J=5.3 and 7.3 Hz, 1H), 4.86 (t, J=6.4 Hz, 1H), 3.93 (s, 3H), 3.88 (s, 3H), 3.21-3.16 (m, 3H), 2.76 (s, 3H), 2.74 (s, 3H), 2.19-2.15 (m, 2H); positive ion ESIMS m/z (rel intensity) 394 [(MH$^+$), 100]. Anal. Calcd for C$_{22}$H$_{23}$N$_3$O$_4$.2HCl.0.5H$_2$O: C, 55.47; H, 5.45; N, 10.59. Found: C, 55.59; H, 5.51; N, 8.84.

7-Aza-5,6-dihydro-6-(3-dimethylaminopropyl)-3-nitro-5,11-dioxo-11H-indeno[1,2-c]isoquinoline Hydrochloride (20)

The general procedure provided the described compound as a bright orange solid (130 mg, 62%): mp 280-282° C. (dec). IR (KBr) 3393, 1705, 1677, 1501, 1338, and 791 cm$^{-1}$; $^1$H NMR (DMSO-d$_6$) δ 9.88 (s, 1H), 8.94 (d, J=2.3 Hz, 1H), 8.74 (dd, J=3.9 and 4.4 Hz, 2H), 8.67 (dd, J=2.5 and 8.9 Hz, 1H), 8.08 (dd, J=1.7 and 6.6 Hz, 1H), 7.60 (dd, J=5.2 and 7.4 Hz, 1H), 4.97 (t, J=6.6, 2 H), 3.26-3.21 (m, 2H), 2.77 (s, 3H), 2.75 (s, 3H), 2.25 (m, 2H); positive ion ESIMS m/z (rel intensity) 379 (MH$^+$, 100). Anal. Calcd for C$_{20}$H$_{18}$N$_4$O$_4$.HCl.1.5H$_2$O: C, 54.36; H, 5.02; N, 12.68. Found: C, 54.13; H, 4.69; N, 12.52.

7-Aza-5,6-dihydro-6-(3-morpholinopropyl)-5,11-dioxo-11H-indeno[1,2-c]isoquinoline Hydrochloride (21)

The general procedure provided the desired compound as an orange solid (255 mg, 62%): mp 316-318° C. IR (KBr) 1704, 1669, 1612, 1570, 1550, 1506, 779 cm$^{-1}$; $^1$HNMR (DMSO-d$_6$) δ 10.40 (s, 1H), 8.61 (d, J=4.5 Hz, 1H), 8.54 (d, J=7.8 Hz, 1H), 7.92 (dd, J=7.2, 1.5 Hz, 1H), 7.86 (t, J=7.2 Hz, 1H), 7.56 (t, J=7.2 Hz, 1H), 7.45 (dd, J=7.5 and 6.6 Hz, 1H), 4.91 (m, 2H), 3.90 (m, 2H), 3.69 (m, 2H), 3.37 (m, 2H), 3.05 (m, 4H), 2.24 (m, 2H). Anal. Calcd for C$_{22}$H$_{21}$N$_3$O$_3$·HCl·1.5H$_2$O: C, 60.20; H, 5.74; N, 9.57. Found: C, 60.37; H, 5.83; N, 9.62.

7-Aza-5,6-dihydro-6-(3-morpholinopropyl)-3-nitro-5,11-dioxo-11H-indeno-[1,2-c]isoquinoline Hydrochloride (23)

The general procedure provided the described compound as a light-red solid (69 mg, 30%): mp 266-228° C. IR (KBr) 1705, 1679, 1614, 1598, 1556, 1502 cm$^{-1}$; $^1$H NMR (DMSO-d$_6$) δ 10.28 (s, 1H), 8.96 (d, J=2.4 Hz, 1H), 8.78-8.75 (m, 2H), 8.67 (dd, J=9.0 and 2.4 Hz, 1H), 8.08 (d, J=7.2 Hz, 1H), 7.60 (dd, J=7.2 and 5.1 Hz, 1H), 4.98 (m, 2H), 3.98 (m, 2H), 3.40 (m, 2H), 3.09 (m, 4H), 2.29 (m, 2H). Anal. Calcd for C$_{22}$H$_{20}$N$_4$O$_5$·0.8H$_2$O: C, 60.77; H, 5.01; N, 12.88. Found: C, 60.92; H, 4.71; N, 12.56.

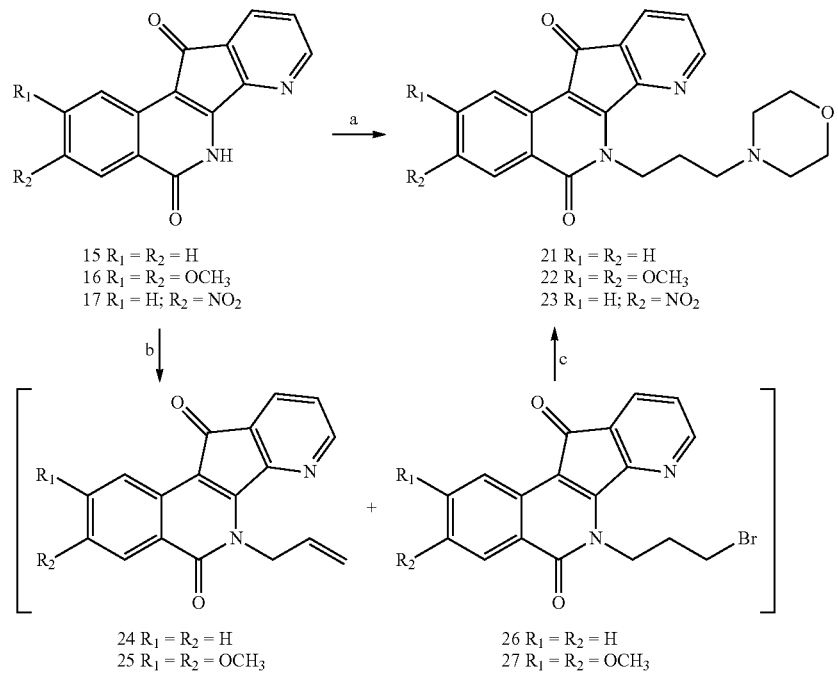

$^a$Reagents and conditions: (a) DIAD, triphenylphosphine, 4-(3-hydroxypropyl)morpholine, THF, 23° C., 3 d (21 62%, 22 68%, 23 30%); (b) NaH, DMF, -5° C. to 23° C., 3 h, 1,3-dibromopropane, -5° C. to 23° C., 12 h; (c) morpholine, 1,4-dioxane, reflux, 6 h (21 15%, 22 17%, 24 13-50%, 25 21-35%).

7-Aza-5,6-dihydro-6-(3-morpholinopropyl)-2,3-dimethoxy-5,11-dioxo-11H-indeno[1,2-c]isoquinolineHydrochloride (22)

The general procedure provided the described compound as a red solid (109 mg, 68%): mp 322-324° C. IR (KBr) 1735, 1704, 1655, 1642, 1607, 1552, 1513 cm$^{-1}$; $^1$H NMR (CDCl$_3$) δ 8.37 (dd, J=5.4 and 1.5 Hz, 1H), 7.86 (s, 1H), 7.61 (dd, J=7.2 and 1.5 Hz, 1H), 7.54 (s, 1H), 7.11 (dd, J=7.2 and 5.1 Hz, 1H), 4.91 (m, 2H), 3.97 (s, 3H), 3.91 (s, 3H), 3.43 (m, 4H), 2.44 (m, 2H), 2.34 (m, 4H), 1.95 (m, 2H); positive ion ESIMS m/z (rel intensity) 436 [(MH$^+$), 100]. Anal. Calcd for C$_{24}$H$_{25}$N$_3$O$_5$·HCl·2.5H$_2$O: C, 55.76; H, 6.04; N, 8.13. Found: C, 55.83; H, 5.87; N, 8.33.

General Procedure for the Preparation of 7-Azaindenoisoquinolines 21-25 and 29-31

Sodium hydride (95%, 50 mg, 2 mmol, 2 equiv) was added to a mixture of the appropriate 7-aza-5,6-dihydro-5,11-dioxo-11H-indeno[1,2-c]isoquinoline (15, 243 mg, 1 mmol, 1 equiv, or 16, 308 mg, 1 mmol, 1 equiv) and DMF (6 mL) at −5° C., and the resulting mixture was allowed to warm to room temperature over 3 h. The resulting clear dark red solution was cooled to −5° C., and 1,3-dibromopropane (788 mg, 4 mmol, 4 equiv) was added. The solution was stirred at room temperature for 12 h. The reaction mixture was quenched with water (50 mL). The products were extracted with chloroform (3-10 mL). The combined extracts were washed with water (3-10 mL), brine (10 mL), dried with sodium sulfate, and concentrated under reduced pressure. The residue was subjected to flash column chromatography (silica gel, CHCl$_3$). The appropriate amine (140.3-200 mg, 2.3 mmol, 2.3 equiv) was added to a solution of crude intermediate in 1,4-dioxane (10 mL). The resulting mixture was heated to reflux for 6 h. The solvent was evaporated under reduced pressure, and the residue was redissolved in chloroform (30 mL). The chloroform solution was washed with water (3-5 mL), brine (5 mL), dried with sodium sulfate, and evaporated to dryness. The solid residue was subjected to flash column chromatography (silica gel), eluting with chloroform, to get 24 and 25, and then with 5-15% methanol in chloroform to obtain 21-23 and 29-31.

7-Aza-5,6-dihydro-6-allyl-5,11-dioxo-11H-indeno[1,2-c]isoquinoline (24)

The general procedure provided the described compound as a red solid (37-150 mg, 13-52%): mp 222-224° C. IR (KBr) 1700, 1666, 1644, 1611, 1568, 1548, 1501 cm$^{-1}$; $^1$H NMR (CDCl$_3$) δ 8.66 (d, J=7.8 Hz, 1H), 8.52 (dd, J=5.1 and 1.5 Hz, 1H), 8.38 (d, J=7.5 Hz, 1H), 7.81-7.73 (m, 2H), 7.52 (t, J=8.1 Hz, 1H), 7.24 (dd, J=7.5 and 5.4 Hz, 1H), 6.11 (m, 1H), 5.67 (d, J=5.7 Hz, 1H), 5.32-5.19 (m, 2H). Anal. Calcd for C$_{18}$H$_{12}$N$_2$O$_2$.0.2H$_2$O: C, 74.06; H, 4.28; N, 9.60. Found: C, 73.97; H, 4.14; N, 9.53.

7-Aza-5,6-dihydro-6-allyl-2,3-dimethoxy-5,11-dioxo-11H-indeno[1,2-c]isoquinoline (25)

The general procedure provided the described compound as a dark-red solid (73-122 mg, 21-35%): mp 266-268° C. IR (KBr) 1701, 1659, 1608, 1570, 1552, 1515 cm$^{-1}$; $^1$H NMR (CDCl$_3$) δ 8.47 (dd, J=5.4, 1.5 Hz, 1H), 8.03 (s, 1H), 7.74-7.71 (m, 2H), 7.18 (dd, J=7.5, 5.4 Hz, 1H), 6.01 (m, 1H), 5.62 (d, J=5.7 Hz, 2H), 5.35.17 (m, 2H), 4.06 (s, 3H), 3.99 (s, 3H). Anal. Calcd for C$_{20}$H$_{16}$N$_2$O$_4$.0.2H$_2$O: C, 68.25; H, 4.70; N, 7.96. Found: C, 61.21; H, 4.63; N, 7.90.

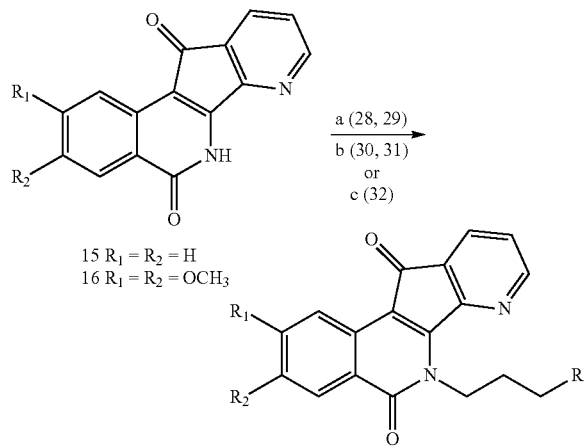

15 R$_1$ = R$_2$ = H
16 R$_1$ = R$_2$ = OCH$_3$

28 R$_1$ = R$_2$ = H; R = 1-imidazolyl
29 R$_1$ = R$_2$ = OCH$_3$; R = 1-imidazolyl
30 R$_1$ = R$_2$ = H; R = NH(CH$_2$)$_2$OH
31 R$_1$ = R$_2$ = OCH$_3$; R = NH(CH$_2$)$_2$OH
32 R$_1$ = R$_2$ = OCH$_3$; R = NH$_2$ $^a$Reagents and conditions: (a) (1) NaH, DMF, -5° C. to 23° C., 3 h, 1,3-dibromopropane, -5° C. to 23° C., 12 h, (2) imidazole, 1,4-dioxane, reflux, 6 h (28 17%, 29 17%); (b) (1) NaH, DMF, -5° C. to 23° C., 3 h, 1,3-dibromopropane, -5° C. to 23° C., 12 h, (2) 2-ethanolamine, 1,4-dioxane, reflux, 6 h (30 16%, 31 20%); (c) (1) NaH, DMF, -5° C. to 23° C., 3 h, 1,3 dibromopropane, -5° C. to 23° C., 12 h, (2) NaN$_3$, DMF, 23° C., 12 h; (3) P(OC$_2$H$_5$)$_3$, benzene, reflux, 6 h; (4) HCl, H$_2$O, reflux, 3 h (32 18%).

7-Aza-5,6-dihydro-6-(3-(1H-imidazol-1-yl)propyl)-5,11-dioxo-11H-indeno[1,2-c]isoquinoline (28)

The general procedure provided the described compound as an orange solid (59 mg, 17%): mp 200-202° C. IR (KBr) 1698, 1664, 1610, 1570, 1549, 1506 cm$^{-1}$; $^1$H NMR (CDCl$_3$) δ 8.64 (d, J=8.1 Hz, 1H), 8.43 (dd, J=5.1, 1.5 Hz, 1H), 8.37 (d, J=7.2 Hz, 1H), 7.80-7.72 (m, 2H), 7.58 (s, 1H), 7.53 (m, 2H), 7.23 (dd, J=7.5, 5.4 Hz, 1H), 7.09 (s, 1H), 7.01 (s, 1H), 5.00 (t, J=7.5 Hz, 2H), 4.17 (t, J=6.9 Hz, 2H), 2.36 (quint, J=7.5 Hz, 2H); positive ESIMS m/z (rel intensity) 357 (MH$^+$, 100). Anal. Calcd for C$_{21}$H$_{16}$N$_4$O$_2$.0.6H$_2$O: C, 68.69; H, 4.72; N, 15.26. Found: C, 68.98; H, 4.62; N, 14.82.

7-Aza-5,6-dihydro-6-(3-(1H-imidazol-1-yl)propyl)-2,3-dimethoxy-5,11-dioxo-11H-indeno[1,2-c]isoquinoline (29)

The general procedure provided the described compound as a purple solid (69 mg, 17%): mp 238-240° C. IR (KBr) 1699, 1649, 1609, 1570, 1552, 1516 cm$^{-1}$; $^1$HNMR (CDCl$_3$) δ 8.38 (dd, J=5.1, 1.5 Hz, 1H), 8.0 (s, 1H), 7.72 (dd, J=7.5, 1.8 Hz, 1H), 7.67 (s, 1H), 7.56 (s, 1H), 7.19 (dd, J=7.5, 5.4 Hz, 1H), 7.07 (s, 1H), 6.99 (s, 1H), 4.96 (t, J=7.5 Hz, 2H), 4.15 (t, J=7.2 Hz, 2H), 4.04 (s, 3H), 3.99 (s, 3H), 2.33 (quint, J=7.2 Hz, 2H); positive ESIMS m/z (rel intensity) 349 (100), 417 (MH$^+$, 61). Anal. Calcd for C$_{23}$H$_{20}$N$_4$O$_4$.0.5H$_2$O: C, 64.93; H, 4.98; N, 13.17. Found: C, 65.13; H, 4.88; N, 12.70.

7-Aza-5,6-dihydro-6-(3-(2-hydroxyethylamino)propyl)-5,11-dioxo-11H-indeno[1,2-c]isoquinoline Hydrochloride (30)

The general procedure provided the described compound. The product was redissolved in chloroform (5 mL), and HCl solution in methanol (3 M, 1 mL) was added. The resulting solution was evaporated to dryness to obtain an orange solid (58 mg, 16%): mp 258-262° C. (dec). IR (KBr) 1711, 1665, 1611, 1569, 1549, 1503 cm$^{-1}$; $^1$H NMR (CDCl$_3$) δ 8.73 (s, 2H), 8.64 (dd, J=5.1, 1.5 Hz, 1H), 8.51 (d, J=7.8 Hz, 1H), 8.24 (d, J=8.1 Hz, 1H), 7.91 (dd, J=7.5, 1.5 Hz, 1H), 7.86 (t, J=7.5 Hz, 1H), 7.59 (t, J=8.1 Hz, 1H), 7.46 (dd, J=7.2, 5.1 Hz, 1H), 4.89 (t, J=6.6 Hz, 2H), 3.63 (t, J=5.1 Hz, 2H), 3.05-2.98 (m, 4H), 2.19 (m, 2H); positive ESIMS m/z (rel intensity) 350 (MH$^+$ 100), 289 (74). Anal. Calcd for C$_{20}$H$_{19}$N$_3$O$_3$.HCl.H$_2$O: C, 59.22; H, 5.52; N, 10.36. Found: C, 58.98; H, 5.02; N, 10.10.

7-Aza-5,6-dihydro-6-(3-(2-hydroxyethylamino)propyl)-2,3-dimethoxy-5,11-dioxo-11H-indeno[1,2-c]isoquinoline Hydrochloride (31)

The general procedure provided the described compound. The product was redissolved in chloroform (5 mL), and HCl solution in methanol (3 M, 1 mL) was added. The resulting solution was evaporated to dryness to obtain a purple solid (83 mg, 20%): mp 280-282° C. (dec). IR (KBr) 1703, 1639, 1609, 1594, 1570, 1553, 1516 cm$^{-1}$; $^1$H NMR (DMSO-d$_6$) δ 8.72 (s, 2H) 8.57 (d, J=5.1 Hz, 1H), 7.83 (s, 1H), 7.81 (d, J=7.5 Hz, 1H), 7.49 (s, 1H), 7.56 (s, 1H), 7.39 (dd, J=7.2, 5.4 Hz, 1H), 5.25 (s, 1H), 4.82 (t, J=6.3 Hz, 2H), 3.90 (s, 3H), 3.86 (s, 3H), 3.63 (s, 2H), 2.98 (s, 4H), 2.16 (m, 2H); positive ESIMS m/z (rel intensity) 410 (MH$^+$, 100). Anal. Calcd for C$_{22}$H$_{23}$N$_3$O$_5$.HCl.H$_2$O: C, 56.96; H, 5.65; N, 9.06. Found: C, 56.65; H, 5.24; N, 9.08.

7-Aza-5,6-dihydro-6-(3-aminopropyl)-2,3-dimethoxy-5,11-dioxo-11H-indeno[1,2-c]isoquinoline Hydrochloride (32)

Sodium hydride (95%, 50 mg, 2 mmol) was added to a mixture of 7-aza-5,6-dihydro-2,3-dimethoxy-5,11-dioxo-11H-indeno[1,2-c]isoquinoline (16, 308 mg, 1 mmol) and DMF (6 mL) at −5° C., and the resulting mixture was allowed to warm to room temperature over 3 h. The resulting clear dark red solution was cooled to −5° C., and 1,3-dibromopropane (788 mg, 4 mmol) was added. The solution was stirred at room temperature for 12 h. The reaction mixture was quenched with water (50 mL). The products were extracted with chloroform (3-10 mL). The combined extracts were washed with water (3-10 mL), brine (10 mL), dried with sodium sulfate, and concentrated under reduced pressure. The residue was subjected to flash column chromatography (silica gel, $CHCl_3$) to provide a mixture of 25 and 27 that was further used without additional purification or separation. Sodium azide (650 mg, 10 mmol) was added to a solution of the mixture of 25 and 27 in DMF (5 mL). The resulting mixture was stirred at room temperature for 12 h. Water (50 mL) was added to the mixture, and the products were extracted with chloroform (3-10 mL). The chloroform solution was washed with water (3-10 mL), brine (10 mL), dried with sodium sulfate, and evaporated to dryness. The residue was redissolved in benzene (10 mL), and triethyl phosphite (332 mg, 2 mmol) was added. The resulting solution was heated to reflux for 6 h. Diluted hydrochloric acid (1 mL) was added to the solution, and the mixture was heated for 3 h and cooled down to room temperature. Potassium hydroxide solution (2%) was added to the mixture to pH 10-12. The organic layer was separated, and the aqueous solution was extracted with ethyl acetate (3-5 mL). The combined organic layers were washed with water (3-10 mL), concentrated potassium carbonate solution (10 mL), dried with sodium sulfate, and evaporated to dryness. The residue was subjected to flash column chromatography (silica gel), eluting with chloroform, to get unreacted 25, and then with 15% methanol in chloroform to obtain a solid product. The product was redissolved in chloroform (5 mL), and HCl solution in methanol (1 mL) was added. The resulting solution was evaporated to dryness to obtain 32 as a purple solid (69 mg, 18%): mp 298-300° C. (dec). IR (KBr) 1703, 1658, 1617, 1570, 1555, 1516 cm$^{-1}$; $^1$H NMR (DMSO-$d_6$) δ 8.60 (dd, J=5.4, 1.5 Hz, 1H), 7.95 (s, 1H), 7.87 (dd, J=7.5, 1.5 Hz, 1H), 7.75 (s, 1H), 7.59 (s, 1H), 7.41 (dd, J=7.5, 5.4 Hz, 1H), 4.89 (t, J=6.3 Hz, 2H), 3.94 (s, 3H), 3.89 (s, 3H), 2.88 (t, J=7.2 Hz, 2H), 2.42 (s, 3H), 2.08 (quint, J=7.0 Hz, 2H); positive ESIMS m/z (rel intensity) 349 (100), 366 (MH$^+$, 72). Anal. Calcd for $C_{20}H_{19}N_3O_4 \cdot HCl \cdot 0.6H_2O$: C, 58.22; H, 4.96; N, 9.95. Found: C, 58.21; H, 5.18; N, 10.18.

Biological Results I

Topoisomerase I Mediated DNA Cleavage Reactions

Human recombinant Top1 was purified from baculovirus as previously described (J. Biol. Chem. 1999, 274, 8516-8523). DNA cleavage reactions were prepared as previously reported with the exception of the DNA substrate (Nat. Protoc. 2008, 3, 1736-1750). Briefly, a 117-bp DNA oligonucleotide (Integrated DNA Technologies) encompassing the previously identified Top1 cleavage sites in the 161-bp fragment from pBluescript SK(−) phagemid DNA was employed. This 117-bp oligonucleotide contains a single 50-cytosine overhang, which was 30-end-labeled by fill-in reaction with [R-$^{32}$P]dGTP in React 2 buffer (50 mMTris-HCl, pH 8.0, 100 mM $MgCl_2$, 50 mM NaCl) with 0.5 unit of DNA polymerase I (Klenow fragment, New England BioLabs). Unincorporated [$^{32}$P]dGTP was removed using mini Quick SpinDNA columns (Roche, Indianapolis, Ind.), and the eluate containing the 30-end-labeled DNA substrate was collected. Approximately 2 nM radiolabeled DNA substrate was incubated with recombinant Top1 in 20 μL of reaction buffer [10 mMTris-HCl (pH 7.5), 50 mM KCl, 5 mM $MgCl_2$, 0.1 mM EDTA, and 15 μg/mL BSA] at 25° C. for 20 min in the presence of various concentrations of compounds. The reactions were terminated by adding SDS (0.5% final concentration) followed by the addition of two volumes of loading dye (80% formamide, 10 mM sodium hydroxide, 1 mM sodium EDTA, 0.1% xylene cyanol, and 0.1% bromphenol blue). Aliquots of each reaction mixture were subjected to 20% denaturing PAGE. Gels were dried and visualized by using a phosphoimager and ImageQuant software (Molecular Dynamics). For simplicity, cleavage sites were numbered as previously described in the 161-bp fragment (J. Biol. Chem. 1999, 274, 8516-8523).

Compounds were tested for induction of DNA damage in Top1-mediated DNA cleavage assays (Nat. Protoc. 2008, 3, 1736-1750). For this purpose, a 32P 30-end-labeled 117-bp DNA fragment was incubated with human recombinant Top1 and increasing concentration of a tested compound. The DNA fragments were separated on a denaturing gel. The Top1 inhibitory activity was assigned based on the visual inspection of the number and intensities of the DNA cleavage bands and expressed in semiquantitative fashion relative to the Top1 inhibitory activities of compounds 1 and 2: 0, no detectable activity; +, weak activity; ++, activity similar to that of 2; +++, activity greater than that of 2; ++++, equipotent to 1 (Table 1). The results for representative indenoisoquinolines 33-34 are provided for comparison.

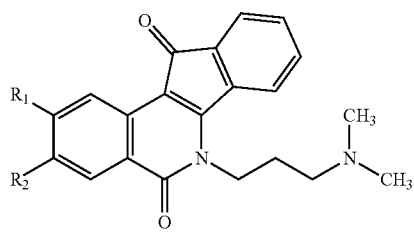

33 $R_1 = R_2 = H$
34 $R_1 = R_2 = OCH_3$
35 $R_1 = H; R_2 = NO_2$

TABLE 1

| | | | | cytotoxicity ($GI_{50}$, μM)[c] | | | | | | |
|---|---|---|---|---|---|---|---|---|---|---|
| Cpd | Top1 Cleavage[a] | $MGM^b$ | lung HOP-62 | colon HCT-116 | CNS SF-539 | melanoma UACC-62 | ovarian OVCAR-3 | renal SN12C | prostate DU-145 | breast MCF7 |
| 1 | ++++ | 0.04 | 0.01 | 0.03 | 0.01 | 0.01 | 0.22 | 0.02 | 0.01 | 0.013 |
| 2 | ++ | 8.51 | 2.82 | 11.48 | 1.66 | 0.56 | 22.39 | 25.70 | 4.79 | 1.91 |
| 18 | +++ | 1.78 | 1.51 | 0.41 | 1.91 | 2.69 | 2.57 | 0.81 | 1.35 | 0.25 |
| 19 | +++ | 4.50 | 3.392 | 1.58 | 4.07 | 13.18 | 3.55 | 3.16 | 1.70 | 0.44 |
| 20 | +++(+) | 1.86 | 2.349 | 0.44 | 2.69 | 3.31 | 2.29 | 1.0 | 0.93 | 0.36 |
| 21 | +(+) | 15.49 | 35.48 | 1.86 | 5.62 | >100 | 28.18 | 5.37 | 3.55 | 2.75 |
| 22 | ++ | 0.30 | 0.30 | 0.22 | 0.29 | 0.095 | 0.37 | 0.52 | 0.31 | 0.052 |
| 23 | +++ | | | | | | | | | |
| 28 | ++ | 7.24 | 7.24 | 1.20 | 5.13 | 35.48 | 8.71 | 3.72 | 2.88 | 3.39 |
| 29 | ++ | | | | | | | | | |
| 30 | + | 1.29 | 1.41 | 0.30 | 0.87 | 3.09 | 1.55 | 0.76 | 0.41 | 0.48 |
| 31 | +(+) | 0.29 | 0.30 | 0.15 | 0.26 | 0.12 | 0.34 | 0.23 | 0.32 | 0.074 |
| 32 | +(+) | 2.09 | 3.02 | 0.38 | 2.19 | 8.13 | 1.58 | 2.88 | 1.62 | 49 |
| 33 | +++ | 1.86 | 1.74 | 0.58 | 1.86 | 0.51 | 1.66 | 0.91 | 1.32 | 0.55 |
| 34 | ++(+) | 6.17 | 11.48 | 2.45 | 6.17 | 6.61 | 5.89 | 10.96 | 4.47 | 6.17 |
| 35 | +++ | 9.77 | 5.62 | 6.46 | | 7.08 | 32.36 | 4.17 | 5.62 | 0.24 |

[a]The relative Top1 inhibitory potencies of the compounds are presented as follows: 0: no detectable activity; +: weak activity; ++: similar activity as compound 2; +++ and ++++: greater activity than compound 2; ++++: similar activity as 1 μM 1.
[b]Mean graph midpoint for growth inhibition of all human cancer cell lines successfully tested.
[c]The cytotoxicity $GI_{50}$ values listed are the concentrations corresponding to 50% growth inhibition, and are the result of single determinations.

The antiproliferative activity of each compound was determined in the National Cancer Institute (NCI) screen (Drug Dev. Res. 1995, 34, 91-109; J. Natl. Cancer Inst. 1990, 82, 1107-1112; Drug Dev. Res. 1995, 34, 91-109). Cells of approximately 60 different human cancer cell lines were incubated for 48 h with five 10-fold dilutions of the tested compounds starting from 100 μM and then treated with sulforhodamine B dye. The ratios of recorded optical densities relative to that of the control were plotted as a function of the common logarithm of the tested compound concentrations. The interpolation between the points located above and below the 50% percentage growth provided respective 50% growth inhibition ($GI_{50}$) values. The $GI_{50}$ and the mean graph midpoint (MGM) values of the prepared indenoisoquinolines in selected cell lines are presented in Table 1.

Determination of Drug Water Solubility.

Water solubility for 18, 19, 33, or 34 was determined by HPLC according to a previously published protocol (Drug Discovery and Evaluation: Safety and Pharmacokinetiks Assay; Springer: New York, 2006; pp 400-402). Solid samples of 18, 19, 33, or 34 (4-10 mg) were weighed and added to 1 M Tris buffer solution (250 μL, pH 7.5). The suspensions were shaken for 24 h at 25° C. and then centrifuged, and the supernatants were filtered. Aliquots (10 μL) of the supernatants were injected into the HPLC system equipped with a C18 reverse-phase column (5 μm, 100 Å, 15 cm×4.6 cm, ES Industries, West Berlin, N.J.), eluting with methanol (1% trifluoroacetic acid)/water [90:10 (v:v)]. One point calibration was done by injecting 10 μL aliquots of the corresponding buffer solutions of 18, 19, 33, or 34 with known concentrations.

The solubilities of two 7-azaindenoisoquinolines were assessed and compared to that of closely related "classical" indenoisoquinolines, as shown below. Aqueous solubility was determined by an HPLC method, as described above. For this test, the samples of two azaindenoisoquinolies and two comparative indenoisoquinolines were shaken with 1M Tris buffer (pH 7.5) solution. The aliquots of the supernatants were injected into the HPLC system after 24 h. In order to determine the concentration of the sample, one point calibration was done against standards with known concentrations of the sample compounds. The estimation of the solubility demonstrated that the introduction of a pyridine ring into the indenoisoquinoline system led to a significant increase of the water solubility. The increase in solubility of the drug did not compromise the Top1 inhibitory activity or cytotoxicity of the drugs: (Table 1).

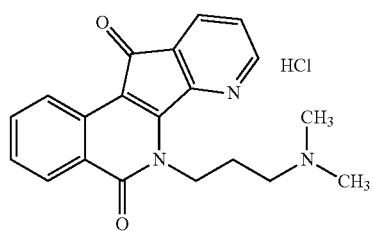

18

Top1 inhibition[a]: +++
Water solubility: 0.024M

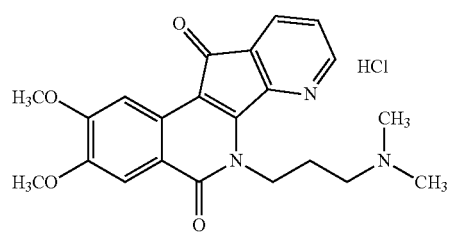

19

Top1 inhibition[a]: +++
Water solubility: 0.1M

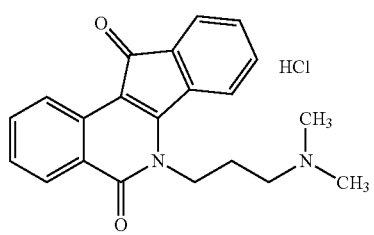

Top1 inhibition[a]: +++
Water solubility: $2.8 \times 10^{-4}$ M

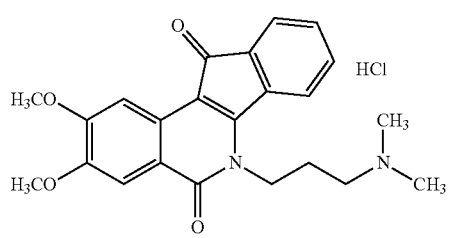

Top1 inhibition[a]: +++
Water solubility: 0.06M

[a]See Table 1, above.

Preparation of 8-azaindenoisoquinolines 17 and 18

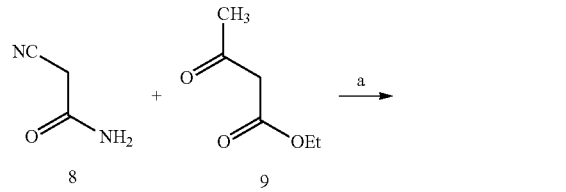

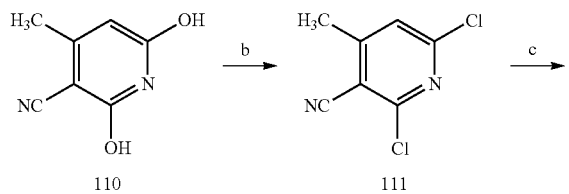

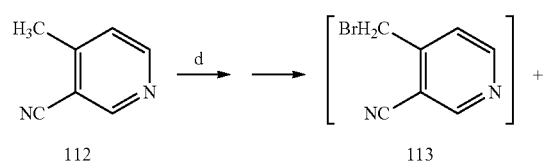

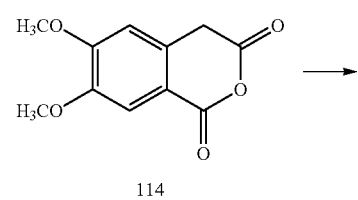

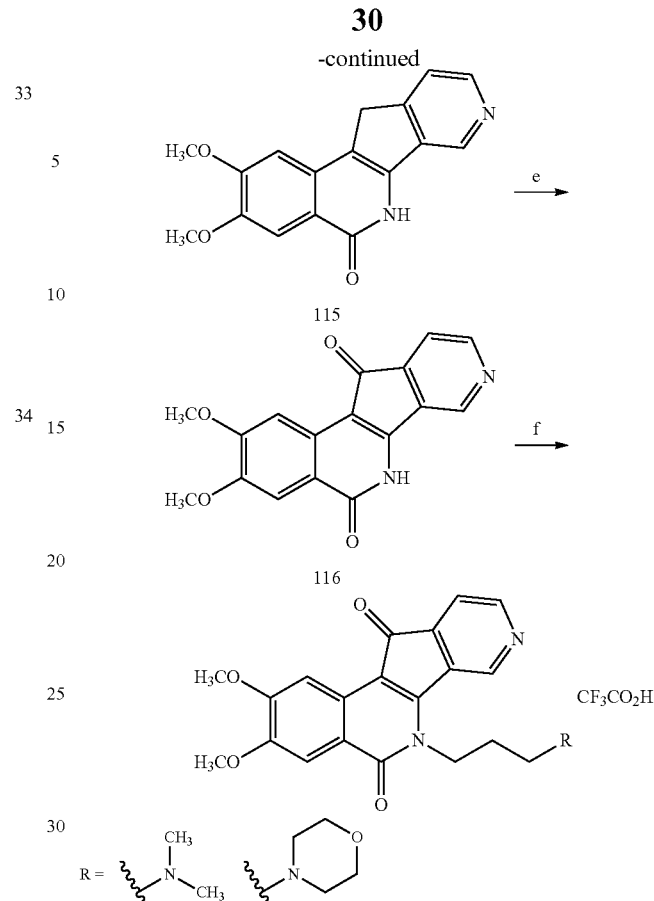

[a]Reagents and conditions: (a) KOH, methanol, reflux, 12 h (75%); (b) POCl₃, sealed tube, 150-180° C., 8 h (67%); (c) H₂, PdCl₂, CH₃CO₂Na, methanol, 23° C., 14 h (93%); (d) (1) NBS, AIBN, CCl₄, reflux, 3.5 h, (2) 114, triethylamine, acetonitrile, reflux 14 h (13%); (e) SeO₂, 1,4-dioxane, reflux, 4 h (49%); (f) (1) DIAD, triphenylphosphine, 3-dimethylamino-1-propanol (for 117) or 4-(3-hydroxypropyl)morpholine (for 118), THF, 23° C., 3 h, (2) TFA, diethyl ether, chloroform, 23° C. (117 34%, 118 35%).

3-Cyano-2,6-dihydroxy-4-methylpyridine (110)

Cyanoacetamide (8, 34 g, 0.40 mol) and ethyl acetoacetate (9, 52 g, 0.40 mol) were dissolved in methanol (250 mL) at room temperature, a solution of potassium hydroxide (28 g, 0.42 mol) in methanol (200 mL) was slowly added, and the resulting mixture was heated to reflux for 12 h. The reaction mixture was cooled to room temperature and the white amorphous precipitate was filtered and washed with methanol (2×50 mL). The solid product was redissolved in hot water. The solution was carefully acidified and the off-white precipitate was allowed to form. The precipitate was filtered and washed with water and methanol to yield 110 (46 g, 75%): mp>300° C. (dec) [lit. (*J. Org. Chem.* 1960, 25, 560-564.) mp 315-320° C. (dec)]. ¹H NMR (300 MHz, DMSO-$d_6$) δ 5.58 (s, 1H), 2.22 (s, 3H).

3-Cyano-2,6-dichloro-4-methylpyridine (111)

3-Cyano-2,6-dihydroxy-4-methylpyridine (110, 10 g, 0.07 mol) and phosphorus oxychloride (25 mL, 0.27 mol) were sealed in a heavy-walled tube and the mixture was heated to 150-180° C. in an oil bath for 8 h. The resulting mixture was allowed to cool to room temperature and carefully quenched by pouring it into ice (200 g). The light brown precipitate was filtered, washed with water and dried to yield 111 (8.3 g, 67%): mp 114-118° C. (lit. (*J. Org. Chem.* 1960, 25, 560-564.) mp 109-110° C.). $^1$H NMR (300 MHz, DMSO-d$_6$) δ 6.77 (s, 1H), 1.49 (s, 3H).

3-Cyano-4-methylpyridine (112)

(*J. Org. Chem.* 1960, 25, 560-564.) Palladium dichloride (50 mg, 0.3 mmol) was added to a degassed solution of 11 (5.0 g, 27 mmol) and sodium acetate (4.5 g, 55 mmol) in methanol (100 mL). The resulting mixture was stirred under hydrogen (1 atm) for 14 h at room temperature. The precipitate was filtered and washed with methanol (3×20 mL). The combined filtrates were evaporated under reduced pressure, and chloroform (50 mL) was added to the residue. The chloroform solution was filtered through a thin pad of silica gel, washing with additional portions of chloroform. The filtrate was evaporated to dryness to provide 112 (2.9 g, 93%) as a yellow oil. $^1$H NMR (300 MHz, DMSO-d$_6$) δ 8.77 (s, 1H), 8.63 (s, J=6.0 Hz, 1H), 7.3 (d, J=6.0 Hz, 1H), 2.56 (s, 3H). 3-Cyano-4-methylpyridine (112) was used further without additional purification.

8-Aza-5,6-dihydro-2,3-dimethoxy-5-oxo-11H-indeno[1,2-c]isoquinoline (115)

3-Cyano-4-methylpyridine (12, 1.5 g, 13 mmol), NBS (3.3 g, 19 mmol) and AIBN (100 mg, 0.6 mmol) were diluted with carbon tetrachloride (60 mL) and the mixture was heated at reflux for 3.5 h. The reaction mixture was concentrated to one-half its original volume, filtered, and the filtrate was evaporated to dryness under reduced pressure. The residue was diluted with acetonitrile (60 mL), 4,5-dimethoxyhomophthalic anhydride (114, 5.6 g, 25 mmol) was added, followed by triethylamine (3.5 mL, 25 mmol), and the solution was heated at reflux for 14 h. The solution was allowed to cool to room temperature, and the precipitate was filtered and washed with acetonitrile (2×15 mL) to provide 115 as a grey solid (500 mg, 13%): mp 270-272° C. IR (KBr) 1633, 1611, 1593 cm$^{-1}$; $^1$H NMR (300 MHz, CDCl$_3$) δ 12.31 (s, 1H), 9.08 (s, 1H), 8.48 (d, J=6.0 Hz, 1H), 7.61 (m, 2H), 7.13 (s, 1H) 3.93 (s, 5H), 3.86 (s, 3H); positive ESIMS m/z (rel intensity): 295 (MH$^+$, 100).

8-Aza-5,6-dihydro-2,3-dimethoxy-5,11-dioxo-11H-indeno[1,2-c]isoquinoline (116)

8-Aza-5,6-dihydro-2,3-dimethoxy-5-oxo-11H-indeno[1,2-c]isoquinoline (115, 250 mg, 0.85 mmol) and SeO$_2$ (190 mg, 1.7 mmol) were diluted with 1,4-dioxane (20 mL) and the mixture was heated at reflux for 4 h. The reaction mixture was filtered while hot, and the precipitate was washed with hot dioxane (3×10 mL). The combined filtrates were evaporated to dryness under reduced pressure. The solid residue was purified by flash column chromatography (silica gel), eluting with 5% methanol in chloroform, to obtain 16 (130 mg, 49%): mp 300-302° C. IR (KBr) 1708, 1648, 1611, 1579 cm$^{-1}$; $^1$H NMR (300 MHz, DMSO-d$_6$) δ 12.96 (s, 1H), 8.56 (d, J=6.2 Hz and 1.4 Hz, 1H), 7.86-7.81 (m, 2H), 7.59 (s, 1H), 7.40 (t, J=6.8 Hz, 1H); positive ESIMS m/z (rel intensity): 309 (MH$^+$, 100).

8-Aza-5,6-dihydro-6-(3-dimethylaminopropyl)-2,3-dimethoxy-5,11-dioxo-11H-indeno[1,2-c]isoquinoline Trifluoroacetate (117)

8-Aza-5,6-dihydro-2,3-dimethoxy-5,11-dioxo-11H-indeno[1,2-c]isoquinoline (116, 92 mg, 0.30 mmol), 3-dimethylamino-1-propanol (0.1 mL, 0.9 mmol), and PPh$_3$ (240 mg, 0.92 mmol) were diluted with THF (15 mL). Diisopropyl azodicarboxylate (0.18 mL, 0.92 mmol) was added to the THF solution, and the resulting mixture was stirred at room temperature for 3 h. The reaction mixture was then evaporated to dryness under reduced pressure. The residue was purified by flash column chromatography (silica gel), eluting with 10% methanol in chloroform, followed by preparative TLC (silica gel), eluting with 5% methanol in chloroform, to provide orange solid. The solid was redissolved in chloroform (5 mL) and trifluoroacetic acid (2 M in diethyl ether, 1 mL) was added. The precipitate was collected by filtration and washed with ether (2×2 mL) to yield the product in the form of its trifluoroacetate salt (53 mg, 34%): mp 230-232° C. (dec). IR (KBr) 1690, 1612 cm$^{-1}$; $^1$H NMR (300 MHz, CD$_3$OD) δ 8.68-8.60 (m, 2H), 7.73 (d, J=5.5 Hz, 1H), 7.69 (s, 1H), 7.26 (s, 1H), 4.57 (t, J=6.1 Hz, 2H), 3.76 (s, 3H), 3.70 (s, 3H), 3.24-3.08 (m, 2H), 2.69 (s, 6H), 2.24-2.06 (m, 2H); positive ion ESIMS m/z (rel intensity): 394 (MH$^+$, 100); HRMS-ESI m/z: MH$^+$ calcd for C$_{22}$H$_{23}$N$_3$O$_4$, 394.1767. found, 394.1769; HPLC purity: 97.44% [C-18 reverse phase, MeOH (1% CF$_3$COOH)/H$_2$O, 80:20].

8-Aza-5,6-dihydro-6-(3-(4-morpholino)propyl)-2,3-dimethoxy-5,11-dioxo-11H-indeno[1,2-c]isoquinoline Trifluoroacetate (118)

8-Aza-5,6-dihydro-2,3-dimethoxy-5,11-dioxo-11H-indeno[1,2-c]isoquinoline (116, 100 mg, 0.32 mmol), 4-(3-hydroxypropyl)-morpholine (94.3 mg, 0.65 mmol), and PPh$_3$ (170 mg, 0.65 mmol) were diluted with THF (10 mL). Diisopropyl azodicarboxylate (0.13 mL, 0.65 mmol) was added to the THF solution and the resulting mixture was stirred at room temperature for 3 h. The reaction mixture was then evaporated to dryness under reduced pressure. The residue was purified by flash column chromatography (silica gel), eluting with 10% methanol in chloroform, followed by preparative TLC (silica gel), eluting with 5% methanol in chloroform, to provide an orange solid. The solid was redissolved in chloroform (5 mL) and trifluoroacetic acid (2 M in diethyl ether, 1 mL) was added. The precipitate was collected by filtration and washed with ether (2×2 mL) to yield the product in the form of its trifluoroacetate salt (62 mg, 35%): mp 213-214° C. IR (KBr) 1778, 1753, 1679, 1614 cm$^{-1}$; $^1$H NMR (300 MHz, DMSO-d$_6$) δ 10.15 (s, 1H), 8.83-8.58 (m, 2H), 7.69 (s, 1H), 7.44 (d, J=4.5 Hz, 1H), 7.31 (s, 1H), 4.69 (t, J=5.8 Hz, 2H), 4.02 (d, J=12.3 Hz, 2H), 3.92 (s, 3H), 3.90 (s, 3H), 3.67 (t, J=11.5 Hz, 2H), 3.54 (d, J=12.1 Hz, 2H), 3.40 (s, 2H), 3.16 (s, 2H), 2.32 (s, 2H); positive ion ESIMS m/z (rel intensity): 436 (MH$^+$, 100); HRMS-ESI m/z: MH$^+$ calcd for C$_{24}$H$_{25}$N$_3$O$_5$, 436.1872. found, 436.1769; HPLC purity: 97.05% [C-18 reverse phase, MeOH (1% CF$_3$COOH)/H$_2$O, 90:10]; 97.36% [C-18 reverse phase, MeOH (1% CF$_3$COOH)/H$_2$O, 70:30].

Preparation of 9-azaindenoisoquinolines 27 and 28

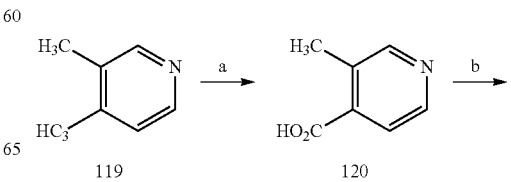

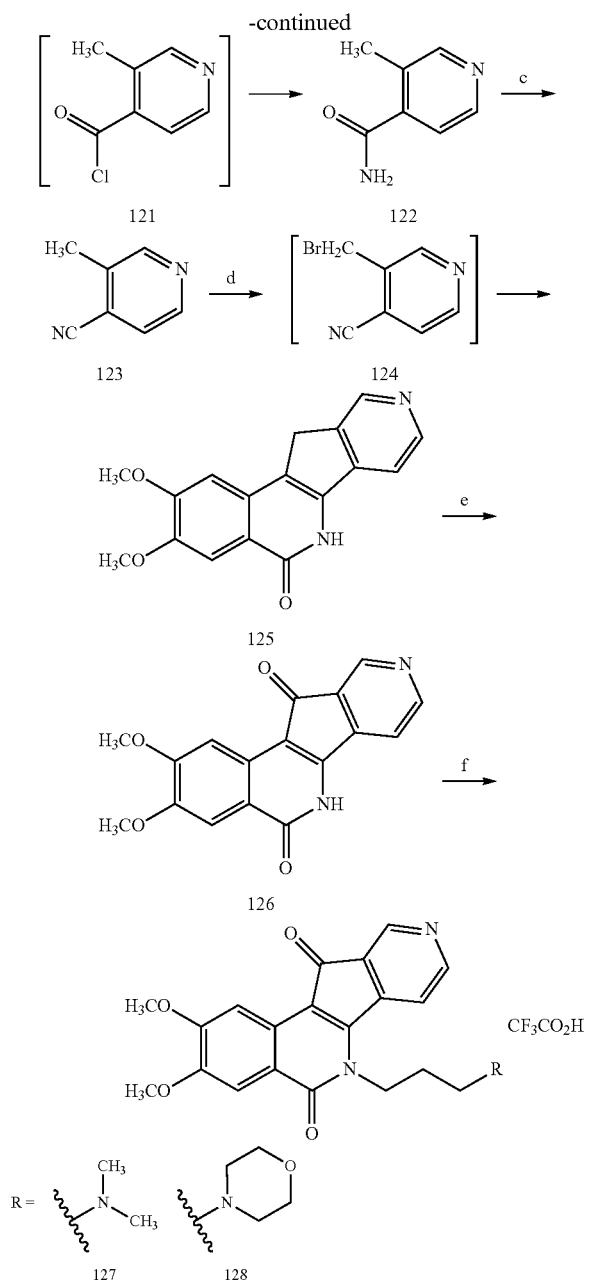

<sup>a</sup>Reagents and conditions: (a) SeO₂, Ph₂O, 180° C., 1 h (47%); (b) (1) SOCl₂, reflux, 3 h, (2) concd aq NH₃, 0-5° C. (60%); (c) POCl₃, reflux, 24 h (90%); (d) (1) NBS, AIBN, CCl₄, reflux, 2 h, (2) 114, triethylamine, acetonitrile, reflux 14 h (14%); (e) SeO₂, 1,4-dioxane, reflux, 4 h (94%); (f) (1) DIAD, triphenylphosphine, 3-dimethylamino-1-propanol (for 27) or 4-(3-hydroxypropyl)morpholine (for 128), THF, 23° C., 3 h, (2) TFA, diethyl ether, chloroform, 23° C. (127 62%, 128 10%).

3-Methyl-4-nicotinic Acid (120)

A solution of 3,4-lutidine (119, 30 g, 0.28 mol) in diphenyl ether (150 mL) was heated to 150-170° C. and selenium dioxide (62 g, 0.56 mol) was carefully added to the hot solution in small portions in the course of 1 h. The resulting mixture was heated to 180° C. for 1 h. The reaction mixture was filtered while hot, and the collected precipitate was washed with boiling water (3×300 mL). The combined filtrates were extracted with chloroform (3×300 mL). The aqueous phase was evaporated to dryness, and the remaining product was recrystallized from ethanol (450 mL) to obtain pure acid 120 (18 g, 47%): mp 220-222° C. (lit. (*J. Chem. Soc., Perkin Trans.* 11984, 1501-1505) mp 232° C.). ¹HNMR (300 MHz, DMSO-d₆) δ 8.59 (s, 1H), 8.04 (s, 1H), 8.47 (d, J=4.8, 1 H), 7.69 (d, J=4.8, 1 H), 2.48 (s, 3H).

3-Methyl-4-nicotinamide (122)

A solution of 3-methyl-4-nicotinic acid (120, 5.0 g, 37 mmol) in thionyl chloride (20 mL, 0.28 mol) was heated at reflux for 3 h. The thionyl chloride was evaporated. The solid acid chloride 121 was added in small portions to a concentrated ammonium hydroxide solution (300 mL) while cooling the reaction mixture to 0-5° C. The reaction mixture was saturated with potassium carbonate, and the solution was extracted with chloroform (2×150 mL) and ethyl acetate (2×150 mL). The aqueous phase was evaporated to dryness, and the resulting solid was extracted with hot ethyl acetate (3×150 mL). The combined extracts were evaporated to dryness to yield crude 122 (3.0 g, 60%): mp 140-142° C. ¹H NMR (300 MHz, DMSO-d₆) δ 8.47 (s, 1H), 8.44 (d, J=4.9 Hz, 1H), 7.94 (s, 1H), 7.65 (s, 1H), 7.29 (d, J=4.9 Hz, 1H), 2.32 (s, 3H).

3-Methyl-4-cyanopyridine (123)

Phosphorus oxychloride (100 mL, 1.1 mol) was slowly added to the crude amide 122 (15 g, 0.11 mol) while cooling the mixture in an ice bath. The resulting solution was heated at reflux for 24 h. The reaction mixture was cooled to room temperature and the excess phosphorus oxychloride was removed under reduced pressure. Crushed ice (150 g) was slowly added to the oily residue, and the solution was neutralized with saturated ammonium hydroxide. The crude product was extracted with chloroform (3×100 mL). The combined extracts were filtered through a layer of silica gel, washing with extra portions of chloroform. The filtrates were evaporated to dryness to yield 123 as colorless crystals (12 g, 90%): mp 45-47° C. (lit. (*J. Med. Chem.* 2000, 43, 3168-3185) mp 50° C.). ¹H NMR (300 MHz, CDCl₃) δ 8.66 (s, 1H), 8.59 (d, J=5.0 Hz, 1H), 7.45 (d, J=5.0 Hz, 1H), 2.54 (s, 3H).

9-Aza-5,6-dihydro-2,3-dimethoxy-5-oxo-11H-indeno[1,2-c]isoquinoline (125)

3-Methylisonicotinonitrile (123, 590 mg, 5.0 mmol), NBS (1.2 g, 7.0 mmol) and AIBN (50 mg, 0.3 mmol) were diluted with carbon tetrachloride (20 mL); and the mixture was heated at reflux for 2 h. The reaction mixture was concentrated to one-half its original volume, filtered, and the filtrate was evaporated to dryness under reduced pressure. The residue was diluted with acetonitrile (25 mL), and 114 (2.2 g, 10 mmol) was added, followed by triethylamine (5 mL, 36 mmol), and the solution was heated at reflux for 14 h. The solution was allowed to cool to room temperature and the precipitate was filtered and washed with acetonitrile (50 mL) to provide a light-brown solid (200 mg, 14%): mp 306-308° C. IR (KBr) 1639, 1613, 1592 cm⁻¹; ¹H NMR (300 MHz, DMSO-d₆) δ 12.32 (s, 1H), 8.73 (s, 1H), 8.54 (d, J=6.0 Hz, 1H), 7.87 (d, J=6.0 Hz, 1H), 7.65 (s, 1H), 7.23 (s, 1H), 3.96 (s, 3H), 3.88 (s, 3H), 3.37 (s, 2H); positive ESIMS m/z (rel intensity): 295 (MH⁺, 100).

9-Aza-5,6-dihydro-2,3-dimethoxy-5,11-dioxo-11H-indeno[1,2-c]isoquinoline (126)

9-Aza-5,6-dihydro-2,3-dimethoxy-5-oxo-11H-indeno[1,2-c]isoquinoline (25, 100 mg, 0.34 mmol) and SeO₂ (75 mg, 0.68 mmol) were diluted with 1,4-dioxane (10 mL) and the mixture was heated at reflux for 4 h. The reaction mixture was filtered while hot and the precipitate was washed with hot dioxane (3×10 mL). The combined filtrates were evaporated to dryness under reduced pressure. The solid residue was purified by flash column chromatography (silica gel), eluting with 5% methanol in chloroform, to obtain 126 (98 mg, 94%): mp 312-314° C. IR (KBr) 1710, 1638, 1608 cm$^{-1}$; $^1$H NMR (300 MHz, DMSO-$d_6$) δ 12.96 (s, 1H), 8.56 (d, J=6.2 Hz and 1.4 Hz, 1H), 7.86-7.81 (m, 2H), 7.59 (s, 1H), 7.40 (t, J=6.8 Hz, 1H); positive ESIMS m/z (rel intensity): 309 (MH$^+$, 100), negative ion ESIMS m/z (rel intensity): 307 [(M-H$^+$)$^-$, 100].

9-Aza-5,6-dihydro-6-(3-dimethylaminopropyl)-2,3-dimethoxy-5,11-dioxo-11H-indeno[1,2-c]isoquinoline Trifluoroacetate (127)

9-Aza-5,6-dihydro-2,3-dimethoxy-5,11-dioxo-11H-indeno[1,2-c]isoquinoline (26, 92 mg, 0.3 mmol), 3-dimethylamino-1-propanol (0.1 mL, 0.9 mmol), and PPh$_3$ (240 mg, 0.92 mmol) were diluted with THF (15 mL). Diisopropyl azodicarboxylate (0.18 mL, 0.92 mmol) was added to the THF solution, and the resulting mixture was stirred at room temperature for 3 h. The reaction mixture was then evaporated to dryness under reduced pressure. The residue was purified by flash column chromatography (silica gel), eluting with 10% methanol in chloroform, to provide a dark-orange solid. The solid was redissolved in chloroform (10 mL), and trifluoroacetic acid (2 M in diethyl ether, 1 mL) was added. The precipitate was collected by filtration and washed with ether (2×2 mL) to yield the product in the form of its trifluoroacetate salt (94 mg, 62%): mp 220° C. (dec). IR (KBr) 1772, 1688, 1633, 1612 cm$^{-1}$; $^1$H NMR (300 MHz, CD$_3$OD) δ 8.61 (d, J=5.2 Hz, 1H), 8.44 (s, 1H), 7.54 (d, J=7.0 Hz, 2H), 7.16 (s, 1H), 4.62 (t, J=6.0 Hz, 2H), 3.84 (s, 3H), 3.81 (s, 3H), 3.40-3.29 (m, 2H), 2.89 (s, 6H), 2.38-2.24 (m, 2H); positive ion ESIMS m/z (rel intensity): 394 (MH$^+$, 100)); HRMS-ESI m/z: MH$^+$ calcd for $C_{22}H_{23}N_3O_4$, 394.1767. found, 394.1770; HPLC purity: 96.18% [C-18 reverse phase, MeOH (1% CF$_3$COOH)/H$_2$O, 70:30]; 97.23% [C-18 reverse phase, MeOH (1% CF$_3$COOH)/H$_2$O, 80:20].

9-Aza-5,6-dihydro-6-(3-(4-morpholino)propyl)-2,3-dimethoxy-5,11-dioxo-11H-indeno[1,2-c]isoquinoline Trifluoroacetate (128)

9-Aza-5,6-dihydro-2,3-dimethoxy-5,11-dioxo-11H-indeno[1,2-c]isoquinoline (26, 85 mg, 0.28 mmol), 4-(3-hydroxypropyl)morpholine (120 mg, 0.84 mmol), and PPh$_3$ (230 mg, 0.84 mmol) were diluted with THF (10 mL). Diisopropyl azodicarboxylate (0.17 mL, 0.84 mmol) was added to the THF solution and the resulting mixture was stirred at room temperature for 3 h. The reaction mixture was then evaporated to dryness under reduced pressure. The residue was purified by flash column chromatography (silica gel), eluting with 10% methanol in chloroform, to provide a dark-orange solid. The solid was redissolved in chloroform (2 mL), and trifluoroacetic acid (2 M in diethyl ether, 1 mL) was added. The precipitate was collected by filtration and washed with ether (2×2 mL) to yield the product in the form of its trifluoroacetate salt (16 mg, 10%): mp 222-224° C. (dec). IR (KBr) 1772, 1712, 1677, 1635, 1612 cm$^{-1}$; $^1$HNMR (300 MHz, CD$_3$OD) δ 8.73 (s, 1H), 8.62 (s, 1H), 8.55 (d, J=8.3 Hz, 1H), 8.24 (d, J=8.0 Hz, 1H), 7.80 (t, J=7.6 Hz, 2H), 7.59 (t, J=7.7 Hz, 1H), 4.75 (d, J=6.4 Hz, 2H), 3.99 (d, J=11.5 Hz, 2H), 3.68 (t, J=12.7 Hz, 2H), 3.50 (d, J=12.2 Hz, 2H), 3.44-3.35 (m, 2H), 3.13-2.98 (m, 2H), 2.36 (td, J=11.7, 5.7 Hz, 2H); positive ion ESIMS m/z (rel intensity): 436 (MH$^+$, 100); HRMS-ESI m/z: MH$^+$ calcd for $C_{20}H_{19}N_3O_2$, 436.1872. found, 436.1870; HPLC purity: 98.14% [C-18 reverse phase, MeOH (1% CF$_3$COOH)/H$_2$O, 70:30]; 96.84% [C-18 reverse phase, MeOH (1% CF$_3$COOH), 100].

Preparation of 10-azaindenoisoquinolines 37 and 38

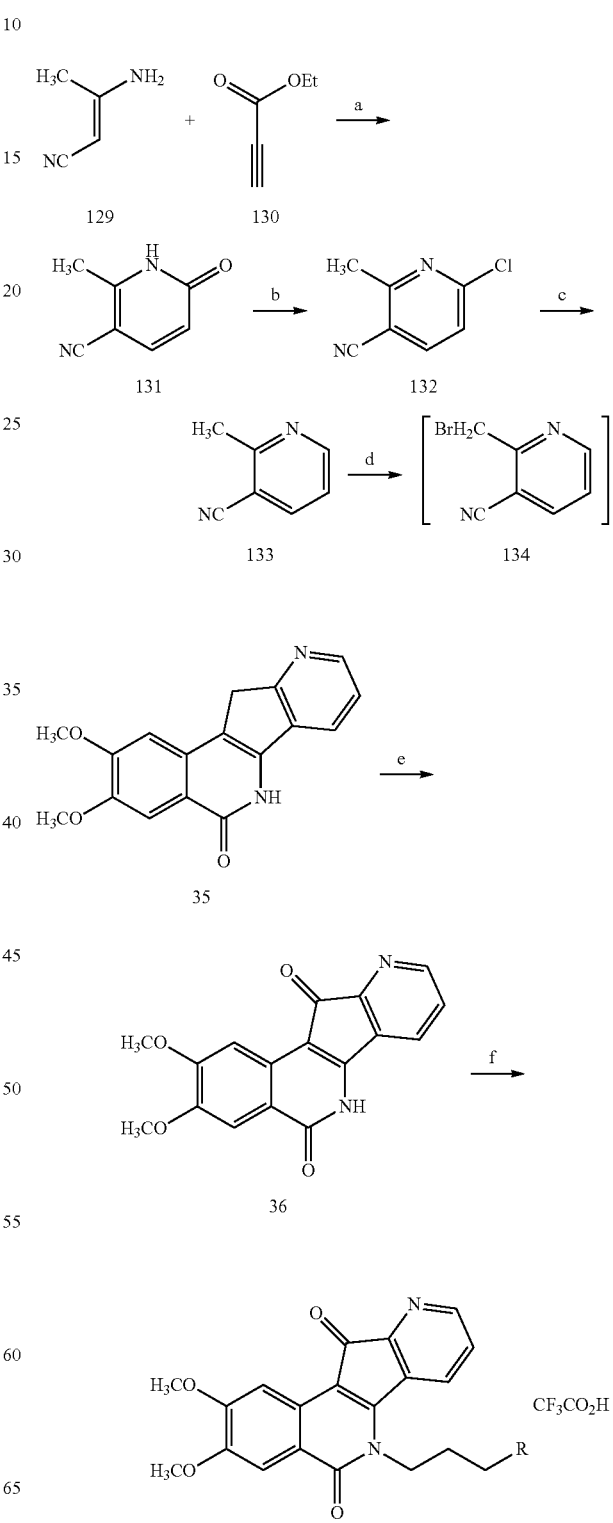

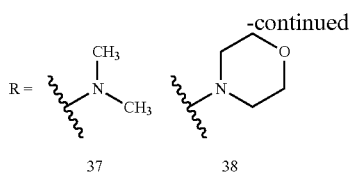

37     38

[a]Reagents and conditions: (a) DMF, reflux, 3 d (31%); (b) POCl₃, reflux, 6 h (54%); (c) HCO₂NH₄, Pd/C, methanol, 23° C., 12 h (81%); (d) (1) NBS, AIBN, 1,2-dichloroethane, reflux, 9 h, (2) 14, triethylamine, acetonitrile, reflux 2 d (31%); (e) SeO₂, 1,4-dioxane, reflux, 3 d (90%); (f) (1) DIAD, triphenylphosphine, 3-dimethylamino-1-propanol (for 37) or 4-(3-hydroxypropyl)morpholine (for 38), THF, 23° C., 12 h, (2) TFA, diethyl ether, chloroform, 23° C. (37 22%, 38 7%).

2-Methyl-6-oxo-1,6-dihydropyridine-3-carbonitrile (131)

(*Synthesis* 1991, 894-896.) 3-Aminocrotonitrile (29, 2.9 g, 36 mmol) and ethyl propiolate (30, 3.0 mL, 36 mmol) were dissolved in dry DMF (17 mL). The reaction mixture was stirred for 1 h at room temperature, and the mixture was heated at reflux for 3 d. The precipitate formed after cooling to room temperature was collected, washed with methanol (5 mL), ether (10 mL), and dried to yield 131 (1.5 g, 31%): mp>300° C. $^1$H NMR (300 MHz, DMSO-$d_6$) δ 12.43 (s, 1H), 7.58 (d, J=9.6 Hz, 1H), 6.23 (d, J=9.6 Hz, 1H), 2.37 (s, 3H).

6-Chloro-2-methylnicotinonitrile (132)

A mixture of 131 (1.5 g, 11 mmol) and phosphorus oxychloride (9 mL, 0.1 mol) was heated at reflux for 6 h. The reaction mixture was cooled to room temperature, and the excess phosphorus oxychloride was removed under reduced pressure. Ice cold water (50 mL) was added to the residue. The brown precipitate was collected and washed with ice cold water (3×25 mL), ether (2×20 mL), and dried to provide 132 as a light-brown solid (0.9 g, 54%): mp 104-105° C. (lit. (*Synthesis* 1991, 894-896) mp 106-108° C.). $^1$HNMR (300 MHz, CDCl₃) δ 7.83 (d, J=8.1 Hz, 1H), 7.29 (d, J=8.1 Hz, 1H), 2.77 (s, 3H).

2-Methylnicotinonitrile (133)

6-Chloro-2-methylnicotinonitrile (132, 10 g, 66 mmol) and ammonium formate (41 g, 0.65 mol) were dissolved in methanol (250 mL), and palladium (5% on activated carbon, 3.5 g, 2.5 mol %) was added. The mixture was stirred at room temperature for 12 h, filtered through Celite, and washed with methanol (3×50 mL). The combined filtrates were evaporated, and the yellow oily residue was subjected to flash column chromatography on silica gel, eluting with chloroform to provide 133 as an off-white solid (6.3 g, 81%): mp 55° C. (lit. (*J. Med. Chem.* 2000, 43, 3168-3185) mp 56-58° C.). $^1$H NMR (300 MHz, CDCl₃) δ 7.80 (dd, J=4.9, 1.6 Hz, 1H), 7.02 (dd, J=7.8, 1.7 Hz, 1H), 6.37 (dd, J=7.8, 5.0 Hz, 1H), 1.88 (s, 3H); positive ion ESIMS m/z (rel intensity): 119 (MH⁺, 100).

10-Aza-5,6-dihydro-2,3-dimethoxy-5-oxo-11H-indenol[1,2-c]isoquinoline (35)

2-Methylnicotinonitrile (133, 3.3 g, 34 mmol), NBS (5.5 g, 33 mmol) and AIBN (600 mg, 4 mmol) were diluted with 1,2-dichloroethane (60 mL) and the mixture was heated at reflux for 9 h. The reaction mixture was concentrated to the half its original volume, filtered, and the filtrate was evaporated to dryness under reduced pressure. The residue was redissolved in acetonitrile (70 mL), 114 (11 g, 48 mmol) was added, followed by triethylamine (7 mL, 50 mmol), and the solution was heated at reflux for 2 d. The hot solution was filtered, and the precipitate was washed with boiling acetonitrile (2×25 mL) to provide a gray solid (2.8 g, 31%): mp 270-272° C. IR (KBr) 1635, 1610, 1528, 1503 cm⁻¹; $^1$HNMR (300 MHz, DMSO-$d_6$) δ 12.26 (s, 1H), 8.40 (d, J=4.9 Hz, 1H), 8.19 (d, J=7.7 Hz, 1H), 7.63 (s, 1H), 7.34 (dd, J=7.6, 5.1 Hz, 1H), 7.19 (s, 1H), 3.95 (s, 3H), 3.91 (s, 2H), 3.86 (s, 3H); positive ESIMS m/z (rel intensity): 295 (M⁺, 100).

10-Aza-5,6-dihydro-2,3-dimethoxy-5,11-dioxo-11H-indeno[1,2-c]isoquinoline (36)

10-Aza-5,6-dihydro-2,3-dimethoxy-5-oxo-11H-indeno[1,2-c]isoquinoline (35, 1.5 g, 5.1 mmol) and SeO₂ (1.13 g, 10.2 mmol) were diluted with 1,4-dioxane (50 mL), and the mixture was heated at reflux for 3 d. The reaction mixture was filtered while hot and the precipitate was extracted in a Soxhlet extractor with chloroform-methanol mixture (4:1). The extracts were evaporated to dryness to afford 36 (1.4 g, 90%): mp>300° C. IR (KBr) 1708, 1659, 1600, 1574 cm⁻¹; $^1$H NMR (300 MHz, DMSO-$d_6$) δ 8.49 (d, J=4.9 Hz, 1H), 8.07 (d, J=7.6 Hz, 1H), 7.83 (s, 1H), 7.56 (s, 1H), 7.42 (dd, J=7.4, 5.2 Hz, 1H), 3.93 (s, 3H), 3.87 (s, 3H); negative ion ESIMS m/z (rel intensity): 307 [(M-H⁺)⁻, 100].

10-Aza-5,6-dihydro-6-(3-dimethylaminopropyl)-2,3-dimethoxy-5,11-dioxo-11H-indeno[1,2-c]isoquinoline Trifluoroacetate (37)

10-Aza-5,6-dihydro-2,3-dimethoxy-5,11-dioxo-11H-indeno[1,2-c]isoquinoline (36, 92 mg, 0.3 mmol), 3-dimethylamino-1-propanol (0.1 mL, 0.9 mmol), and PPh₃ (240 mg, 0.92 mmol) were diluted with THF (15 mL). Diisopropyl azodicarboxylate (0.18 mL, 0.92 mmol) was added to the THF solution, and the resulting mixture was stirred at room temperature for 12 h. The reaction mixture was then evaporated to dryness under reduced pressure. The residue was purified by flash column chromatography (silica gel), eluting with 10% methanol in chloroform, followed by preparative TLC (silica gel), eluting with 5% methanol in chloroform, to provide an orange solid. The solid was redissolved in chloroform (5 mL) and trifluoroacetic acid (2 M in diethyl ether, 1 mL) was added. The precipitate was collected by filtration and washed with ether (2×2 mL) to yield the product in the form of its trifluoroacetate salt (34 mg, 22%): mp 212-214° C. (dec). $^1$H NMR (300 MHz, DMSO-$d_6$) δ 10.60 (s, 1H), 8.50 (dd, J=5.1, 1.3 Hz, 1H), 7.83 (dd, J=7.5, 1.3 Hz, 1H), 7.73 (s, 1H), 7.41 (dd, J=7.5, 5.1 Hz, 1H), 7.32 (s, 1H), 4.67 (t, J=6.1 Hz, 2H), 3.93 (s, 3H), 3.90 (s, 3H), 3.34-3.25 (m, 2H), 2.81 (d, J=4.7 Hz, 6H), 2.38-2.28 (m, 2H); positive ion ESIMS m/z (rel intensity): 394 (MH⁺, 100); HRMS-ESI m/z: MH⁺ calcd for $C_{22}H_{23}N_3O_4$, 394.1767. found, 394.1769; HPLC purity: 98.32% [C-18 reverse phase, MeOH (1% CF₃COOH)/H₂O, 80:20].

10-Aza-5,6-dihydro-6-[3-(4-morpholino)propyl]-2,3-dimethoxy-5,11-dioxo-11H-indeno[1,2-c]isoquinoline Trifluoroacetate (38)

10-Aza-5,6-dihydro-2,3-dimethoxy-5,11-dioxo-11H-indeno[1,2-c]isoquinoline (36, 100 mg, 0.32 mmol), 4-(3-hydroxypropyl)-morpholine (94 mg, 0.65 mmol), and PPh₃ (170 mg, 0.65 mmol) were diluted with THF (10 mL). Diisopropyl azodicarboxylate (130 mg, 0.65 mmol) was added to the THF solution, and the resulting mixture was stirred at room temperature for 12 h. The reaction mixture was then evaporated to dryness under reduced pressure. The residue was purified by flash column chromatography (silica gel), eluting with 10% methanol in chloroform, followed by preparative TLC (silica gel), eluting with 5% methanol in chloroform, to provide an orange solid. The solid was redissolved in chloroform (5 mL) and trifluoroacetic acid (2 M in diethyl ether, 1 mL) was added. The precipitate was collected by filtration and washed with ether (2×2 mL) to yield the product in the form of its trifluoroacetate salt (12 mg, 7%): mp 208-210° C. $^1$H NMR (300 MHz, DMSO-d$_6$) δ 11.05 (s, 1H), 8.51 (d, J=4.0 Hz, 1H), 7.88 (d, J=7.4 Hz, 1H), 7.81 (s, 1H), 7.44 (dd, J=7.4, 5.1 Hz, 1H), 7.40 (s, 1H), 4.71 (t, J=5.8 Hz, 2H), 3.96 (t, J=10.8 Hz, 8H), 3.81 (dd, J=20.1, 8.5 Hz, 2H), 3.50 (d, J=12.1 Hz, 2H), 3.11 (dd, J=21.2, 9.3 Hz, 4H), 2.41-2.33 (m, 2H); positive ion ESIMS m/z (rel intensity): 436 (MH$^+$, 100); HRMS-ESI m/z: MH$^+$ calcd for C$_{24}$H$_{25}$N$_3$O$_5$, 436.1872. found, 436.1769; HPLC purity: 98.28% [C-18 reverse phase, MeOH (1% CF$_3$COOH)/H$_2$O, 90:10]; 97.14% [C-18 reverse phase, MeOH (1% CF$_3$COOH)/H$_2$O, 70:30].

Preparation of 10-azaindenoisoquinolines 45 and 46

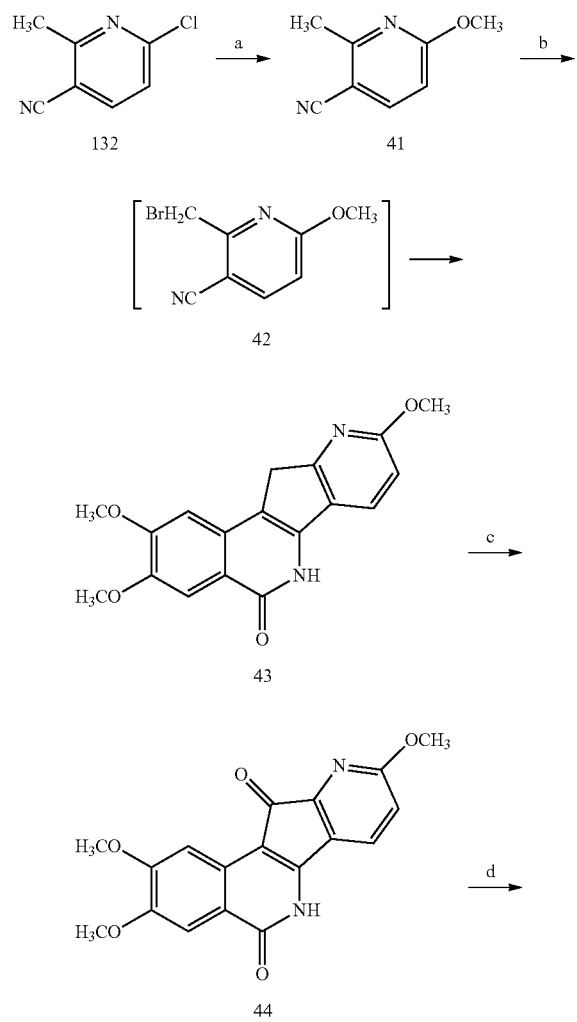

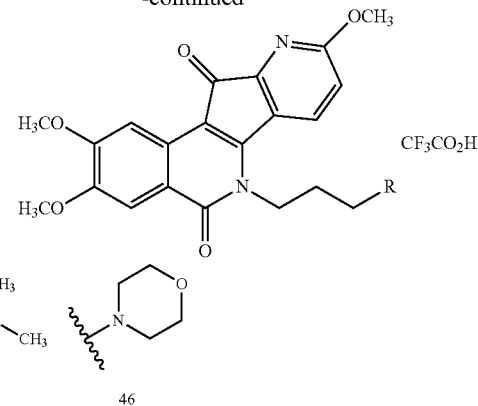

$^a$Reagents and conditions: (a) NaOCH$_3$, methanol, reflux, 1.5 h (87%); (b) (1) NBS, AIBN, 1,2-dichloroethane, reflux, 3.5 h, (2) 114, triethylamine, acetonitrile, reflux 14 h (19%); (c) SeO$_2$, 1,4-dioxane, reflux, 24 h (89%); (d) DIAD, triphenylphosphine, 3-dimethylamino-1-propanol (for 45) or 4-(3-hydroxypropyl)morpholine (for 46), THF, 23° C., 3 d, (2) TFA, diethyl ether, chloroform, 23° C. (45 30%, 46 31%).

6-Methoxy-2-methylnicotinonitrile (41)

Sodium methoxide (20 g, 0.4 mol) was added to a solution of 6-chloro-2-methylnicotinonitrile (132, 10 g, 66 mmol) in methanol (150 mL), and the mixture was heated at reflux for 1.5 h and cooled to room temperature. The precipitate was removed by filtration, and the filtrate was concentrated to dryness. The crude solid was redissolved in chloroform; and the resulting solution was filtered through a layer of silica gel, washing with extra portions of chloroform. The combined filtrates were evaporated to dryness to yield 41 (8.3 g, 87%): mp 81-82° C. (lit. (Synthesis 1991, 894-896) mp 80-80.5° C.). $^1$HNMR (300 MHz, CDCl$_3$) δ 7.66 (d, J=8.5 Hz, 1H), 6.59 (d, J=8.5 Hz, 1H), 3.94 (s, 3H), 2.62 (s, 3H).

10-Aza-5,6-dihydro-2,3,9-trimethoxy-5-oxo-11H-indeno[1,2-c]isoquinoline (43)

6-Methoxy-2-methylnicotinonitrile (41, 2.2 g, 15 mmol), NBS (2.9 g, 16 mmol) and AIBN (100 mg, 0.6 mmol) were diluted with 1,2-dichloroethane (50 mL), and the mixture was heated at reflux for 3.5 h. The reaction mixture was concentrated to one-half its original volume, filtered, and the filtrate was evaporated to dryness under reduced pressure. The residue was diluted with acetonitrile (60 mL); and 114 (5.3 g, 24 mmol) was added, followed by triethylamine (3.5 mL, 25 mmol); and the solution was heated at reflux for 14 h. The solution was allowed to cool to room temperature, and the obtained precipitate was filtered and washed with acetonitrile (2×15 mL) to provide 43 as an off-white solid (0.9 g, 19%): mp 284-286° C. IR (KBr) 1648, 1614 cm$^{-1}$; $^1$H NMR (300 MHz, DMSO-d$_6$) δ 12.20 (s, 1H), 8.14 (d, J=8.4 Hz, 1H), 7.61 (s, 1H), 7.10 (s, 1H), 6.81 (d, J=8.5 Hz, 1H), 3.94 (s, 3H), 3.91 (s, 3H), 3.86 (s, 3H), 3.85 (s, 2H); EIMS m/z: 324 (M$^+$); CIMS m/z (rel intensity): 325 (MH$^+$, 100).

10-Aza-5,6-dihydro-2,3,9-trimethoxy-5,11-dioxo-11H-indeno[1,2-c]isoquinoline (44)

10-Aza-5,6-dihydro-2,3,9-trimethoxy-5-oxo-11H-indeno[1,2-c]isoquinoline (43, 0.7 g, 2.2 mmol) and SeO$_2$ (0.48 mg, 4.3 mmol) were diluted with 1,4-dioxane (50 mL), and the mixture heated at reflux for 24 h. The reaction mixture was filtered while hot, and the precipitate was washed with hot dioxane (3×100 mL). The combined filtrates were evaporated to dryness under reduced pressure to obtain 44 (0.65 g, 89%): mp>350° C. IR (KBr) 1713, 1645, 1624, 1612, 1592 cm$^{-1}$; Negative ion ESIMS m/z (rel intensity): 337 [(M-H$^+$)$^-$, 100].

10-Aza-5,6-dihydro-6-(3-dimethylaminopropyl)-2,3,9-trimethoxy-5,11-dioxo-11H-indeno[1,2-c]isoquinoline Trifluoroacetate (45)

10-Aza-5,6-dihydro-2,3,9-trimethoxy-5,11-dioxo-11H-indeno[1,2-c]isoquinoline (44, 110 mg, 0.32 mmol) was added to a stirred solution of PPh$_3$ (170 mg, 0.65 mmol) and diisopropyl azodicarboxylate (0.13 mL, 0.65 mmol) in tetrahydrofuran (10 mL). The mixture was stirred at room temperature until the solid material completely disappeared to form a dark-red solution. 3-Dimethylamino-1-propanol (67 mg, 0.65 mmol) was added dropwise to the resulting solution over the course of 30 min, and the reaction mixture was stirred at room temperature for 3 d. The resulting mixture was evaporated to dryness under reduced pressure. The residue was purified by flash column chromatography (silica gel), eluting with 3% methanol in chloroform, to provide a red solid. The solid was redissolved in chloroform (10 mL) and trifluoroacetic acid (2 M in diethyl ether, 1 mL) was added. The precipitate was collected by filtration and washed with ether (2×2 mL) to yield the product in the form of its trifluoroacetate salt (52 mg, 30%): mp 250-252° C. (dec). IR (KBr) 1692, 1621, 1605 1562 cm$^{-1}$; $^1$H NMR (500 MHz, CD$_3$OD) δ 7.28 (d, J=8.1 Hz, 1H), 7.16 (s, 1H), 6.95 (s, 1H), 6.54 (d, J=8.1 Hz, 1H), 4.57 (t, J=5.8 Hz, 2H), 3.94 (s, 3H), 3.83 (s, 3H), 3.82 (s, 3H), 3.58-3.48 (m, 2H), 3.07 (s, 6H), 2.46-2.32 (m, 2H); positive ion ESIMS m/z (rel intensity): 424 (MH$^+$, 100). Anal. Calcd for C$_{25}$H$_{26}$F$_3$N$_3$O$_7$: C, 55.87; H, 4.88; N, 7.82. Found: C, 55.45; H, 4.62; N, 7.75.

10-Aza-5,6-dihydro-6-(3-(4-morpholino)propyl)-2,3,9-trimethoxy-5,11-dioxo-11H-indeno[1,2-c]isoquinoline Trifluoroacetate (46)

10-Aza-5,6-dihydro-2,3,9-trimethoxy-5,11-dioxo-11H-indeno[1,2-c]isoquinoline (44, 110 mg, 0.32 mmol) was added to a stirred solution of PPh$_3$ (170 mg, 0.65 mmol) and diisopropyl azodicarboxylate (0.13 mL, 0.65 mmol) in tetrahydrofuran (10 mL). The mixture was stirred at room temperature until the solid material completely disappeared to form a dark-red solution. 4-(3-Hydroxypropyl)morpholine (94 mg, 0.65 mmol) was added dropwise to the resulting solution over the course of 30 min, and the reaction mixture was stirred at room temperature for 3 d. The resulting mixture was evaporated to dryness under reduced pressure. The residue was purified by flash column chromatography (silica gel), eluting with 3% methanol in chloroform, to provide a red solid. The solid was redissolved in chloroform (10 mL) and hydrochloric acid (2 M in methanol, 1 mL) was added. The precipitate was collected by filtration and washed with ether (2×2 mL) to yield the product in the form of its trifluoroacetate salt (61 mg, 31%): mp 237-238° C. (dec). IR (KBr) 1709, 1618, 1605, 1561 cm$^{-1}$; $^1$H NMR (300 MHz, DMSO-d$_6$) δ 10.81 (s, 1H), 7.79 (d, J=8.2 Hz, 1H), 7.70 (s, 1H), 7.33 (s, 1H), 6.86 (d, J=8.2 Hz, 1H), 4.68 (s, 2H), 4.00 (s, 2H), 3.94 (s, 3H), 3.92 (s, 3H), 3.90 (s, 3H), 3.78 (t, J=11.8 Hz, 2H), 3.62-3.40 (m, 4H), 3.18-3.04 (m, 2H), 2.35 (s, 2H); positive ion ESIMS m/z (rel intensity): 466 (MH$^+$, 100); HRMS-ESI m/z: MH$^+$ calcd for C$_{25}$H$_{27}$N$_3$O$_6$, 466.1978. found, 466.1980; HPLC purity: 96.75% [C-18 reverse phase, MeOH (1% CF$_3$COOH)/H$_2$O, 70:30]; 95.27% [C-18 reverse phase, MeOH (1% CF$_3$COOH)].

Preparation of 7-azaindenoisoquinolines 55 and 56

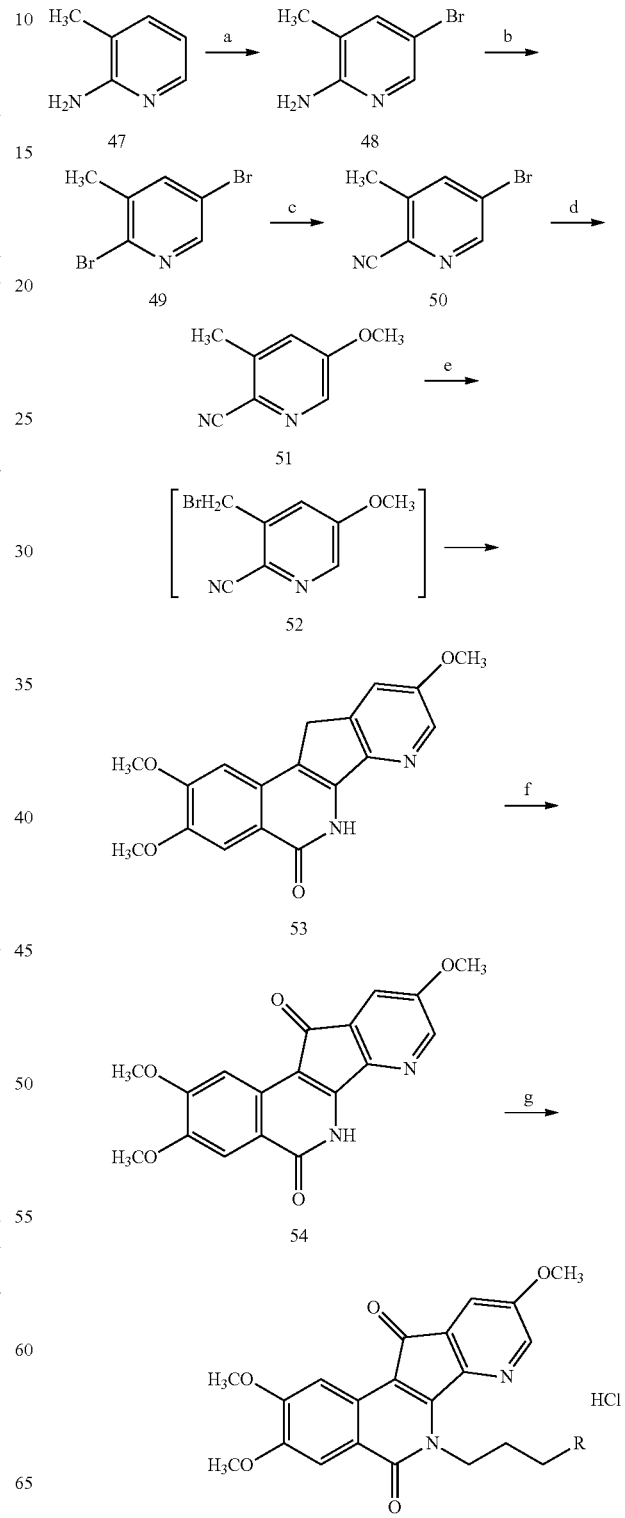

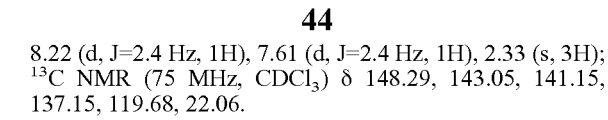

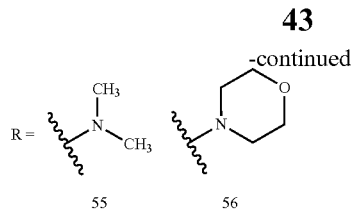

*Reagents and conditions: (a) NBS, CH₃CO₂NH₄, acetonitrile, 0-23° C., 25 min (65%); (b) Br₂, NaNO₂, aq HBr -15° C., then 23° C., 3 h (94%); (c) CuCN, DMF, reflux, 2 h (74%); (d) NaOCH₃, methanol, reflux, 12 h (79%); (e) (1) NBS, AIBN, 1,2-dichloroethane, reflux, 24 h, (2) 114, triethylamine, acetonitrile, reflux 24 h (21%); (f) SeO₂, 1,4-dioxane, reflux, 24 h (92%); (g) (1) DIAD, triphenylphosphine, 3-dimethylamino-1-propanol (for 55) or 4-(3-hydroxypropyl)morpholine (for 56), THF, 23° C., 2 d, (2) HCl, methanol, chloroform, 23° C. (55 52%, 56 59%).

5-Bromo-3-methylpyridin-2-amine (48)

(*J. Mol. Catal. A: Chem.* 2007, 267, 30-33.) N-Bromosuccinimide (170 g, 0.95 mol) was added to a solution of 47 (99 g, 0.92 mol) and ammonium acetate (7 g, 10 mol %) in acetonitrile (500 mL). The temperature of the reaction mixture during addition was controlled with an ice bath. After the full amount of NBS was added, the ice bath was removed and the reaction mixture was stirred at room temperature for 25 min, and acetonitrile was removed under reduced pressure. A mixture of ethyl acetate (1 L) and water (1 L) was added to the solid residue. The resulting mixture was stirred and the organic layer was separated. The water layer was extracted with ethyl acetate (3×500 mL). The combined extracts were washed with water (300 mL), saturated sodium bicarbonate solution (500 L), dried with sodium sulfate and evaporated to dryness to give a dark brown solid. The crude product was redissolved in chloroform (300 mL); and the solution was filtered through a thin pad of silica gel, eluting with chloroform. The combined filtrates were evaporated under reduced pressure to yield 48 as a light-brown solid (113 g, 65%): mp 89-90° C. (lit. (*J. Am. Chem. Soc.* 1976, 98, 1478-1486) mp 91-93° C.). $^1$H NMR (300 MHz, CDCl₃) δ 7.97 (d, J=2.3 Hz, 1H), 7.36 (d, J=2.3 Hz, 1H), 4.50 (s, 2H), 2.09 (s, 3H); $^{13}$C NMR (75 MHz, CDCl₃) δ 156.10, 146.29, 140.03, 118.79, 108.58, 77.72, 77.30, 76.88, 17.27.

2,5-Dibromo-3-methylpyridine (49)

(*J. Med. Chem.* 2007, 50, 3730-3742.) 5-Bromo-3-methylpyridin-2-amine (48, 69 g, 0.37 mol) was suspended in hydrobromic acid (200 mL, 48% in water), and the mixture was cooled to −15° C. Bromine (95 g, 0.59 mol) was added dropwise to the mixture, followed by addition of sodium nitrite (69 g, 1 mol) in water (100 mL). Temperature of the reaction mixture was kept below −15° C. during addition. After addition, the cooling bath was removed and the reaction mixture was stirred for 3 h. The reaction mixture was cooled to −15° C. and quenched with potassium hydroxide (112 g, 2 mol) in water (500 mL). The cooling bath was removed, and the mixture was stirred for 1.5 h. The products were extracted with ethyl acetate (3×300 mL). The combined extracts were washed with water (2×200 mL), saturated aqueous sodium bicarbonate (200 mL), dried with sodium sulfate, and evaporated to dryness. The oily residue was redissolved in chloroform (100 mL), and the solution was filtered through a pad of silica gel, washing with chloroform. The combined filtrates were evaporated to provide 49 as light-yellow solid (87 g, 94%): mp 38-40° C. (lit. (*Recl. Trav. Chim. Pays-Bas* 1965, 84, 951-964) mp 41-42° C.). $^1$H NMR (300 MHz, CDCl₃) δ 8.22 (d, J=2.4 Hz, 1H), 7.61 (d, J=2.4 Hz, 1H), 2.33 (s, 3H); $^{13}$C NMR (75 MHz, CDCl₃) δ 148.29, 143.05, 141.15, 137.15, 119.68, 22.06.

5-Bromo-3-methylpicolinonitrile (50)

Copper(I) cyanide (21 g, 0.24 mol) was added to a solution of 2,5-dibromo-3-methylpyridine (49, 60 g, 0.24 mol) in dry DMF (200 mL), and the mixture was heated at reflux for 2 h. After cooling to room temperature, water (1500 mL) was added to the mixture and the products were extracted with ethyl acetate (3×300 mL). The combined extracts were washed with water (3×300 mL), brine (300 mL), dried with sodium sulfate and evaporated to dryness. The brown oily residue was subjected to flash column chromatography (silica gel), eluting with chloroform, to yield 50 as a white solid (35 g, 74%): mp 86-88° C. $^1$H NMR (300 MHz, CDCl₃) δ 8.55 (d, J=1.8 Hz, 1H), 7.84 (d, J=1.5 Hz, 1H), 2.53 (s, 3H); $^{13}$C NMR (75 MHz, CDCl₃) δ 149.75, 140.68, 139.95, 132.25, 124.61, 115.90, 18.59; EIMS m/z 196/198 (M⁺); CIMS 197/199 (MH⁺). The $^1$H NMR spectrum is consistent with previously published data (*Bioorg. Med. Chem.* 1999, 7, 1845-1855).

5-Methoxy-3-methylpicolinonitrile (51)

5-Bromo-3-methylpicolinonitrile (50, 35 g, 0.18 mol) was added to a solution of sodium methoxide (18 g, 0.54 mol) in methanol (200 mL), and the mixture was heated at reflux for 12 h. The solution was cooled to room temperature and concentrated to one third of its volume. The concentrated solution was diluted with water (150 mL), and the products were extracted with chloroform (3×50 mL). The combined extracts were washed with water (2×50 mL), brine (50 mL), dried with sodium sulfate and filtered through a pad of silica gel, washing with chloroform, to produce 51 as an off-white solid (21 g, 79%): mp 80-81° C. IR (film) 2225, 1645, 1589 cm⁻¹; $^1$H NMR (300 MHz, CDCl₃) δ 8.06 (d, J=2.6 Hz, 1H), 7.03 (d, J=2.4 Hz, 1H), 3.83 (s, 3H), 2.43 (s, 3H); $^{13}$C NMR (75 MHz, CDCl₃) δ 157.65, 139.99, 137.68, 125.05, 120.52, 116.76, 55.84, 18.71; EIMS m/z (rel intensity): 148 (M⁺, 100); CIMS m/z (rel intensity): 149 (MH⁺, 100).

7-Aza-5,6-dihydro-2,3,9-trimethoxy-5-oxo-11H-indeno[1,2-c]isoquinoline (53)

5-Methoxy-3-methylpicolinonitrile (51, 5.0 g, 34 mmol), NBS (6.6 g, 37 mmol) and AIBN (500 mg, 3 mmol) were diluted with 1,2-dichloroethane (50 mL), and the mixture was heated at reflux for 24 h. The reaction mixture was concentrated to one-half its original volume, filtered, and the filtrate was evaporated to dryness under reduced pressure. The residue was redissolved in acetonitrile (100 mL), 4,5-dimethoxy-homophthalic anhydride (14, 11.2 g, 50 mmol) was added, followed by triethylamine (8 mL, 58 mmol), and the solution was heated at reflux for 24 h. The hot solution was filtered, and the precipitate was washed with boiling acetonitrile (2×25 mL) to provide 53 as a gray solid (2.4 g, 21%): mp>260° C. IR (KBr) 1635, 1608 cm⁻¹; $^1$H NMR (300 MHz, DMSO-d₆) δ 11.94 (s, 1H), 8.22 (d, J=2.6 Hz, 1H), 7.63 (s, 2H), 7.17 (s, 1H), 3.95 (s, 3H), 3.89 (s, 3H), 3.87 (s, 3H), 3.85 (s, 2H); positive ion ESIMS m/z (rel intensity): 265 (MH⁺, 100).

7-Aza-5,6-dihydro-2,3,9-trimethoxy-5,11-dioxo-11H-indeno[1,2-c]isoquinoline (54)

10-Aza-5,6-dihydro-2,3,9-trimethoxy-5-oxo-11H-indenol[1,2-c]isoquinoline (53, 2.08 g, 6.4 mmol) and SeO₂ (1.42 g, 12.8 mmol) were diluted with 1,4-dioxane (100 mL), and the mixture was heated at reflux for 24 h. The reaction mixture was filtered while hot and the precipitate was washed with hot dioxane (2×500 mL). The combined filtrates were evaporated to dryness under reduced pressure to afford 54 (2.0 g, 92%): mp>300° C. IR (KBr) 1705, 1662, 1615, 1602, 1563 cm$^{-1}$. Negative ion ESIMS m/z (rel intensity): 339 [(M-H$^+$)$^-$, 100]. The product was introduced into the next step without additional purification.

7-Aza-5,6-dihydro-6-(3-dimethylaminopropyl)-2,3, 9-trimethoxy-5,11-dioxo-11H-indeno[1,2-c]isoquinoline Hydrochloride (55)

7-Aza-5,6-dihydro-2,3,9-trimethoxy-5,11-dioxo-11H-indeno[1,2-c]isoquinoline (54, 338 mg, 1 mmol) was added to a stirred solution of PPh$_3$ (510 mg, 1.9 mmol) and diisopropyl azodicarboxylate (390 mg, 1.9 mmol) in tetrahydrofuran (10 mL). The mixture was stirred for 4 h at room temperature. 3-Dimethylamino-1-propanol (200 mg, 1.9 mmol) was added dropwise to the resulting solution over the course of 30 min, and the reaction mixture was stirred at room temperature for 12 h. PPh$_3$ (510 mg, 1.9 mmol) and diisopropyl azodicarboxylate (390 mg, 1.9 mmol) were added to the reaction mixture. The mixture was stirred for 6 h, and 3-dimethylamino-1-propanol (200 mg, 1.9 mmol) was added, forming a dark red solution. The solution was stirred at room temperature for 24 h and evaporated to dryness under reduced pressure. The residue was subjected to flash column chromatography (silica gel), eluting with a gradient of 1% to 5% methanol in chloroform, to provide a red solid. The solid was redissolved in chloroform (10 mL) and hydrochloric acid (1 M in methanol, 1 mL) was added. The precipitate was collected by filtration and washed with ether (2×2 mL) to yield the product 55 in the form of its hydrochloride salt (238 mg, 52%): mp 245° C. (dec). IR (KBr) 3445, 1699, 1651, 1611 cm$^{-1}$; $^1$H NMR (300 MHz, DMSO-d$_6$) δ 9.90 (s, 1H), 8.21 (s, 1H), 7.81 (s, 1H), 7.49 (s, 1H), 7.43 (s, 1H), 4.78 (s, 2H), 3.94 (s, 3H), 3.91 (s, 3H), 3.86 (s, 3H), 3.15 (s, 2H), 2.76 (s, 3H), 2.74 (s, 3H), 2.14 (s, 2H); positive ion ESIMS m/z (rel intensity): 424 (MH$^+$, 100); HRMS-ESI m/z: MH$^+$ calcd for C$_{23}$H$_{25}$N$_3$O$_5$, 424.1822. found, 424.1869; HPLC purity: 98.61% [C-18 reverse phase, MeOH]; 97.99% [C-18 reverse phase, MeOH/H$_2$O, 85:15].

7-Aza-5,6-dihydro-6-[3-(4-morpholino)propyl]-2,3, 9-trimethoxy-5,11-dioxo-11H-indeno[1,2-c]isoquinoline Hydrochloride (56)

7-Aza-5,6-dihydro-2,3,9-trimethoxy-5,11-dioxo-11H-indeno[1,2-c]isoquinoline (54, 338 mg, 1 mmol) was added to a stirred solution of PPh$_3$ (510 mg, 1.9 mmol) and diisopropyl azodicarboxylate (390 mg, 1.9 mmol) in tetrahydrofuran (10 mL). The mixture was stirred for 4 h at room temperature. 4-(3-Hydroxy-propyl)morpholine (280 mg, 1.9 mmol) was added dropwise to the resulting solution over the course of 30 min, and the reaction mixture was stirred at room temperature for 12 h. PPh$_3$ (510 mg, 1.9 mmol) and diisopropyl azodicarboxylate (390 mg, 1.9 mmol) were added to the reaction mixture. The mixture was stirred for 6 h, and 4-(3-hydroxypropyl)-morpholine (280 mg, 1.9 mmol) was added, forming a dark red solution. The solution was stirred at room temperature for 24 h and evaporated to dryness under reduced pressure. The residue was subjected to flash column chromatography (silica gel), eluting with a gradient of 1% to 5% methanol in chloroform, to provide a red solid. The solid was redissolved in chloroform (10 mL), and hydrochloric acid (1 M in methanol, 1 mL) was added. The precipitate was collected by filtration and washed with chloroform (20 mL) and diethyl ether (10 mL) to yield the product in the form of its hydrochloride salt (276 mg, 59%): mp 260-261° C. (dec). $^1$H NMR (300 MHz, DMSO-d$_6$) δ 8.18 (d, J=2.6 Hz, 1H), 7.76 (s, 1H), 7.45 (s, 1H), 7.38 (d, J=2.6 Hz, 1H), 4.76 (s, 2H), 3.93 (s, 3H), 3.90 (s, 3H), 3.84 (s, 3H), 3.75 (t, J=11.6 Hz, 4H), 3.20 (s, 2H), 3.06 (s, 4H), 2.20 (s, 2H); positive ion ESIMS m/z (rel intensity): 466 (MH+, 100); HRMS-ESI m/z: MH$^+$ calcd for C$_{23}$H$_{25}$N$_3$O$_5$, 466.1978. found, 466.1974; HPLC purity: 95.45% [C-18 reverse phase, MeOH]; 96.67% [C-18 reverse phase, MeOH/H$_2$O, 85:15].

Preparation of 7-azaindenoisoquinolines 63-66

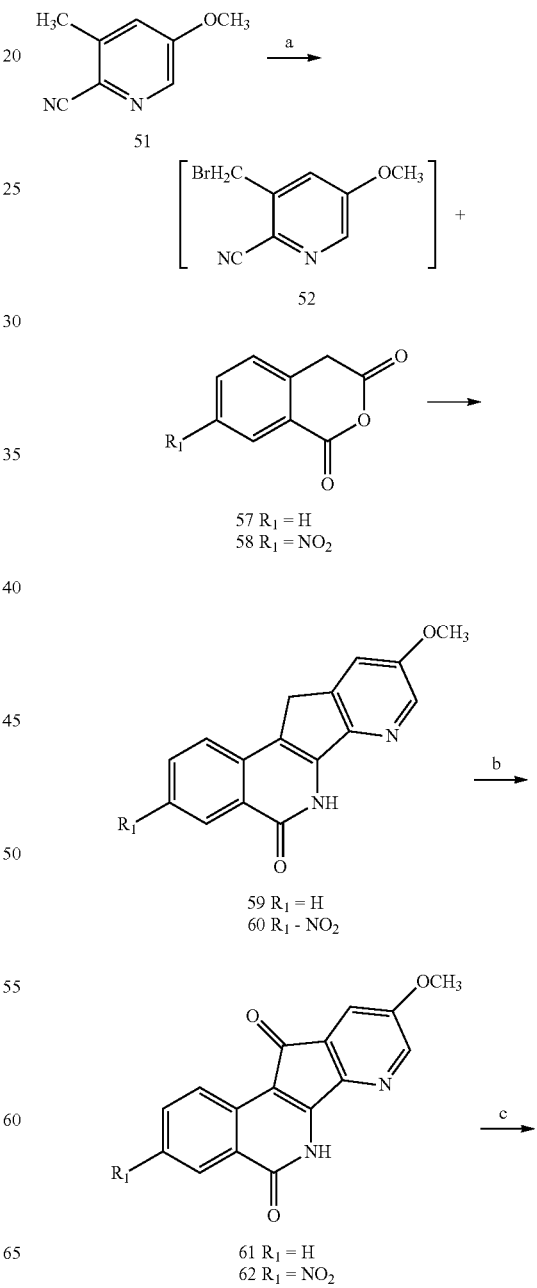

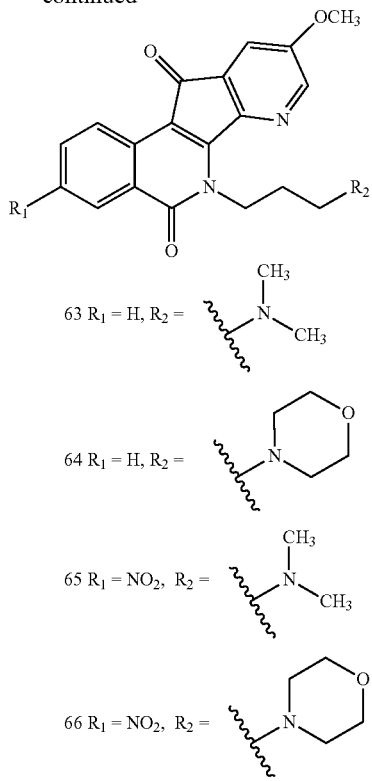

63 R₁ = H, R₂ = –N(CH₃)₂

64 R₁ = H, R₂ = morpholino

65 R₁ = NO₂, R₂ = –N(CH₃)₂

66 R₁ = NO₂, R₂ = morpholino

<sup>a</sup>Reagents and conditions: (a) (1) NBS, AIBN, 1,2-dichloroethane, reflux, 24 h, (2) homophthalic anhydride (57, for 59) or 5-nitrohomophthalic anhydride (58, for 60), triethylamine, acetonitrile, reflux 24 h (59 46%, 60 26%); (e) SeO₂, 1,4-dioxane, reflux, 24 h (61 76%, 62 86%); (d) DIAD, triphenylphosphine, 3-dimethylamino-1-propanol (for 63 and 65) or 4-(3-hydroxypropyl)morpholine (for 64 and 66), THF, 23° C., 2 d (63 38%, 64 40%, 65 61%, 66 47%).

7-Aza-5,6-dihydro-9-methoxy-5-oxo-11H-indenol[1,2-c]isoquinoline (59)

5-Methoxy-3-methylpicolinonitrile (51, 5.0 g, 34 mmol), NBS (6.6 g, 37 mmol) and AIBN (500 mg, 3 mmol) were diluted with 1,2-dichloroethane (50 mL), and the mixture was heated at reflux for 24 h. The reaction mixture was concentrated to one-half its original volume, filtered, and the filtrate was evaporated to dryness under reduced pressure. The residue was redissolved in acetonitrile (100 mL); and homophthalic anhydride (57, 9 g, 55 mmol) was added, followed by triethylamine (8 mL, 58 mmol); and the solution was heated at reflux for 24 h. The hot solution was filtered, and the precipitate was washed with boiling acetonitrile (2×30 mL) to provide 59 as a gray solid (4.1 g, 46%): mp 232-233° C. IR (KBr) 1666, 1621, 1607 cm⁻¹; ¹H NMR (300 MHz, DMSO-d₆) δ 12.11 (s, 1H), 8.29-8.19 (m, 2H), 7.75 (d, J=4.1 Hz, 2H), 7.68 (s, 1H), 7.48 (dd, J=8.1, 4.3 Hz, 1H), 3.89 (s, 5H); positive ion ESIMS m/z (rel intensity): 310 (MH⁺, 100).

7-Aza-5,6-dihydro-3-nitro-9-methoxy-5-oxo-11H-indeno[1,2-c]isoquinoline (60)

5-Methoxy-3-methylpicolinonitrile (51, 5.0 g, 34 mmol), NBS (6.6 g, 37 mmol) and AIBN (500 mg, 3 mmol) were diluted with 1,2-dichloroethane (50 mL), and the mixture was the mixture was heated at reflux for 24 h. The reaction mixture was concentrated to one-half its original volume, filtered, and the filtrate was evaporated to dryness under reduced pressure. The residue was redissolved in acetonitrile (100 mL) and 5-nitrohomophthalic anhydride (58, 11 g, 53 mmol) was added, followed by triethylamine (8 mL, 58 mmol); and the solution was heated at reflux for 24 h. The hot solution was filtered, and the precipitate was washed with boiling acetonitrile (2×30 mL) to provide 60 as a gray solid (2.7 g, 26%): mp>260° C. IR (KBr) 1690, 1616, 1559 cm⁻¹; ¹H NMR (300 MHz, DMSO-d₆) δ 8.89 (d, J=2.5 Hz, 1H), 8.47 (dd, J=8.8, 2.5 Hz, 1H), 8.30 (d, J=2.6 Hz, 1H), 7.91 (d, J=8.8 Hz, 1H), 7.72 (d, J=2.5 Hz, 1H), 3.94 (s, 2H), 3.91 (s, 3H); positive ion ESIMS m/z (rel intensity): 310 (MH⁺, 100).

7-Aza-5,6-dihydro-9-methoxy-5,11-dioxo-11H-indeno[1,2-c]isoquinoline (61)

7-Aza-5,6-dihydro-9-methoxy-5-oxo-11H-indeno[1,2-c]isoquinoline (59, 2.64 g, 10 mmol) and SeO₂ (2.22 g, 20 mmol) were diluted with 1,4-dioxane (120 mL), and the mixture was heated at reflux for 24 h. The reaction mixture was filtered while hot, and the precipitate was washed with hot dioxane (3×300 mL). The combined filtrates were evaporated to dryness under reduced pressure to afford 61 (2.10 g, 76%): mp>350° C. IR (KBr) 1717, 1689, 1618, 1574 cm⁻¹. The product was introduced into the next step without additional purification.

7-Aza-5,6-dihydro-3-nitro-9-methoxy-5,11-dioxo-11H-indeno[1,2-c]isoquinoline (62)

7-Aza-5,6-dihydro-3-nitro-9-methoxy-5-oxo-11H-indeno[1,2-c]isoquinoline (60, 2.2 g, 7 mmol) and SeO₂ (1.6 g, 14 mmol) were diluted with 1,4-dioxane (100 mL), and the mixture was heated at reflux for 24 h. The reaction mixture was filtered while hot and the precipitate was washed with hot dioxane (2×500 mL). The combined filtrates were evaporated to dryness under reduced pressure to yield 62 (1.94 g, 86%): mp>300° C. IR (KBr) 1693, 1618, 1571 cm⁻¹. Negative ion ESIMS m/z (rel intensity): 322 [(M-H⁺)⁻, 100]. The product was introduced into the next step without additional purification.

7-Aza-5,6-dihydro-6-(3-dimethylaminopropyl)-9-methoxy-5,11-dioxo-11H-indeno[1,2-c]isoquinoline (63)

7-Aza-5,6-dihydro-9-methoxy-5,11-dioxo-11H-indeno[1,2-c]-isoquinoline (61, 278 mg, 1 mmol) was added to a stirred solution of PPh₃ (510 mg, 1.9 mmol) and diisopropyl azodicarboxylate (390 mg, 1.9 mmol) in tetrahydrofuran (20 mL). The mixture was stirred at room temperature for 4 h. 3-Dimethylamino-1-propanol (200 mg, 1.9 mmol) was added dropwise to the resulting solution over the course of 15 min, and the reaction mixture was stirred at room temperature for 12 h. PPh₃ (510 mg, 1.9 mmol) and diisopropyl azodicarboxylate (390 mg, 1.9 mmol) were added to the reaction mixture. The mixture was stirred for 6 h, and 3-dimethylamino-1-propanol (200 mg, 1.9 mmol) was added, forming an orange solution. The solution was stirred at room temperature for 24 h and evaporated to dryness under reduced pressure. The residue was subjected to flash column chromatography (silica gel), eluting with a gradient of 1% to 5% methanol in chloroform, to provide 63 as an orange solid (138 mg, 38%): mp 190-192° C. ¹H NMR (300 MHz, CDCl₃) δ 8.35 (d, J=8.1 Hz, 1H), 8.16 (d, J=8.1 Hz, 1H), 7.93 (d, J=2.7 Hz, 1H), 7.59-7.49 (m, 1H), 7.35-7.27 (m, 1H), 7.09 (d, J=2.7 Hz, 1H), 4.82-4.69 (m, 2H), 3.81 (s, 3H), 2.40 (t, J=7.1 Hz, 2H), 2.18 (s, 6H), 1.89 (dt, J=14.6, 7.5 Hz, 2H); positive ion ESIMS m/z (rel intensity): 364 (MH+, 100); HRMS-ESI m/z: MH+ calcd for $C_{20}H_{21}N_3O_3$, 364.1661. found, 364.1663; HPLC purity: 98.39% [C-18 reverse phase, MeOH]; 98.46% [C-18 reverse phase, MeOH/$H_2O$, 85:15].

7-Aza-5,6-dihydro-6-(3-(4-morpholino)propyl)-9-methoxy-5,11-dioxo-11H-indeno[1,2-c]isoquinoline (64)

7-Aza-5,6-dihydro-9-methoxy-5,11-dioxo-11H-indeno[1,2-c]-isoquinoline (61, 278 mg, 1 mmol) was added to a stirred solution of $PPh_3$ (510 mg, 1.9 mmol) and diisopropyl azodicarboxylate (390 mg, 1.9 mmol) in tetrahydrofuran (20 mL). The mixture was stirred at room temperature for 4 h. 4-(3-Hydroxypropyl)morpholine (280 mg, 1.9 mmol) was added dropwise to the resulting solution over the course of 15 min, and the reaction mixture was stirred at room temperature for 12 h. $PPh_3$ (510 mg, 1.9 mmol) and diisopropyl azodicarboxylate (390 mg, 1.9 mmol) were added to the reaction mixture. The mixture was stirred for 6 h, and 4-(3-hydroxypropyl)morpholine (280 mg, 1.9 mmol) was added, forming an orange solution. The solution was stirred at room temperature for 24 h and evaporated to dryness under reduced pressure. The residue was subjected to flash column chromatography (silica gel), eluting with a gradient of 1% to 5% methanol in chloroform, to provide an orange solid (163 mg, 40%): mp 218-224° C. (dec). $^1$H NMR (300 MHz, DMSO-$d_6$) δ 8.45 (d, J=8.2 Hz, 1H), 8.25 (d, J=2.5 Hz, 1H), 8.20 (d, J=7.8 Hz, 1H), 7.82 (t, J=7.7 Hz, 1H), 7.61-7.45 (m, 2H), 4.82 (s, 2H), 3.92 (d, J=12.6 Hz, 5H), 3.74 (t, J=11.9 Hz, 2H), 3.39 (d, J=12.2 Hz, 2H), 3.21 (s, 2H), 3.03 (d, J=11.8 Hz, 2H), 2.22 (s, 2H); positive ion ESIMS m/z (rel intensity): 406 (MH+, 100); HRMS-ESI m/z: MH+ calcd for $C_{20}H_{21}N_3O_3$, 406.1767. found, 406.1773; HPLC purity: 97.30% [C-18 reverse phase, MeOH]; 98.60% [C-18 reverse phase, MeOH/$H_2O$, 85:15].

7-Aza-5,6-dihydro-6-(3-dimethylaminopropyl)-9-methoxy-3-nitro-5,11-dioxo-11H-indeno[1,2-c]isoquinoline (65)

7-Aza-5,6-dihydro-9-methoxy-3-nitro-5,11-dioxo-11H-indeno[1,2-c]isoquinoline (62, 323 mg, 1 mmol) was added to a stirred solution of $PPh_3$ (510 mg, 1.9 mmol) and diisopropyl azodicarboxylate (390 mg, 1.9 mmol) in tetrahydrofuran (20 mL). The mixture was stirred at room temperature for 4 h. 3-Dimethylamino-1-propanol (200 mg, 1.9 mmol) was added dropwise to the resulting solution over the course of 15 min, and the reaction mixture was stirred at room temperature for 12 h. $PPh_3$ (510 mg, 1.9 mmol) and diisopropyl azodicarboxylate (390 mg, 1.9 mmol) were added to the reaction mixture. The mixture was stirred for 6 h, and 3-dimethylamino-1-propanol (200 mg, 1.9 mmol) was added, forming an orange solution. The solution was stirred at room temperature for 24 h and evaporated to dryness under reduced pressure. The residue was subjected to flash column chromatography (silica gel), eluting with a gradient of 1% to 5% methanol in chloroform, to provide 65 as a red solid (250 mg, 61%): mp 224-226° C. $^1$H NMR (300 MHz, $CDCl_3$) δ 9.17 (d, J=2.2 Hz, 1H), 8.71 (d, J=8.8 Hz, 1H), 8.45 (dd, J=8.9, 2.4 Hz, 1H), 8.21 (d, J=2.8 Hz, 1H), 7.41 (d, J=2.8 Hz, 1H), 5.12-4.88 (m, 2H), 3.98 (d, J=4.0 Hz, 3H), 2.48 (t, J=7.0 Hz, 2H), 2.22 (d, J=3.9 Hz, 6H), 1.99 (dt, J=14.3, 7.1 Hz, 2H); positive ion ESIMS m/z (rel intensity): 409 (MH+, 100); HRMS-ESI m/z: MH+ calcd for $C_{20}H_{20}N_4O_5$, 409.1512. found, 409.15101; HPLC purity: 100% [C-18 reverse phase, MeOH]; 99.03% [C-18 reverse phase, MeOH/$H_2O$, 85:15].

7-Aza-5,6-dihydro-6-(3-(4-morpholino)propyl)-9-methoxy-3-nitro-5,11-dioxo-11H-indeno[1,2-c]isoquinoline (66)

7-Aza-5,6-dihydro-9-methoxy-3-nitro-5,11-dioxo-11H-indeno[1,2-c]isoquinoline (62, 323 mg, 1 mmol) was added to a stirred solution of $PPh_3$ (510 mg, 1.9 mmol) and diisopropyl azodicarboxylate (390 mg, 1.9 mmol) in tetrahydrofuran (20 mL). The mixture was stirred at room temperature for 4 h. 4-(3-Hydroxypropyl)morpholine (280 mg, 1.9 mmol) was added dropwise to the resulting solution over the course of 15 min, and the reaction mixture was stirred at room temperature for 12 h. $PPh_3$ (510 mg, 1.9 mmol) and diisopropyl azodicarboxylate (390 mg, 1.9 mmol) were added to the reaction mixture. The mixture was stirred for 6 h, and 4-(3-hydroxypropyl)morpholine (280 mg, 1.9 mmol) was added, forming an orange solution. The solution was stirred at room temperature for 24 h and evaporated to dryness under reduced pressure. The residue was subjected to flash column chromatography (silica gel), eluting with a gradient of 1% to 5% methanol in chloroform, to provide 66 as a red solid (212 mg, 47%): mp 243-245° C. (dec). $^1$H NMR (300 MHz, DMSO-$d_6$) δ 8.81 (s, 1H), 8.55 (s, 2H), 8.32 (d, J=2.5 Hz, 1H), 7.59 (d, J=2.5 Hz, 1H), 4.84 (s, 2H), 3.96 (s, 3H), 3.79 (s, 4H), 3.21 (m, 6H), 2.22 (s, 2H); positive ion ESIMS m/z (rel intensity): 451 (MH+, 100); HPLC purity: 95.42% [C-18 reverse phase, MeOH]; 95.93% [C-18 reverse phase, MeOH/$H_2O$, 85:15].

Biological Results II

All of the target compounds were tested for induction of DNA damage in Top1-mediated DNA cleavage assays, as described above. The Top1 inhibitory activity was assigned based on the visual inspection of the number and intensities of the DNA cleavage bands and expressed in semiquantitative fashion relative to the Top1 inhibitory activities of compounds 1 (camptothecin) and 2 (NSC 316622): 0, no detectable activity; +, weak activity; ++, similar activity to compound 2; +++, greater activity than 2; ++++, equipotent to 1 (Table 2).

The antiproliferative activity of each compound was determined in the National Cancer Institute (NCI) screen as described above. Cells of approximately 60 different human cancer cell lines were incubated for 48 h with five 10-fold dilutions of the test compounds starting from 100 μM, and then treated with sulforhodamine B dye. The ratios of recorded optical densities relative to those of the control were plotted as a function of the common logarithm of the tested compound concentrations. The interpolation between the points located above and below the 50% percentage growth provided 50% growth inhibition ($GI_{50}$) values. The $GI_{50}$ and the mean graph midpoint (MGM) values of the prepared (aza)indenoisoquinolines in selected cell lines are presented in Table 2. The MGM is based on a calculation of the average $GI_{50}$ for all of the cell lines tested in which $GI_{50}$ values above and below tested range ($10^{-4}$ to $10^{-8}$ M) are taken as the maximum ($10^{-4}$ M) and minimum ($10^{-8}$ M) drug concentrations used in the screening test. The Top1 inhibitory and cytotoxicity (MGM and $GI_{50}$) data for 1 (camptothecin) and 2 (NSC 316622) and 7-azaindenoisoquinolines listed in Table 1, above as 19 and 22 are included in Table 2 for comparison purposes.

TABLE 2

Top1 Inhibitory and Antiproliferative Activity of Azaindenoisoquinolines.

| | | | | | cytotoxicity (GI$_{50}$, μM)$^c$ | | | | | |
|---|---|---|---|---|---|---|---|---|---|---|
| Cpd | Top1 Cleavage$^a$ | MGM$^b$ | lung HOP-62 | colon HCT-116 | CNS SF-539 | melanoma UACC-62 | ovarian OVCAR-3 | renal SN12C | prostate DU-145 | breast MCF7 |
| 2 | ++ | 8.5 | 2.8 | 11.5 | 1.7 | 0.56 | 22 | 26 | 4.8 | 1.9 |
| 1 | ++++ | 0.040 | 0.010 | 0.030 | 0.010 | 0.010 | 0.22 | 0.020 | 0.010 | 0.013 |
| 19 | +++ | 4.5 | 3.4 | 1.6 | 4.1 | 13 | 3.6 | 3.2 | 1.7 | 0.44 |
| 22 | ++ | 0.30 | 0.30 | 0.22 | 0.29 | 0.10 | 0.37 | 0.52 | 0.31 | 0.052 |
| 117 | ++ | ND$^d$ | ND | ND | ND | ND | ND | ND | ND | ND |
| 118 | ++ | 16 | 6.5 | 2.5 | 40 | 48 | 24 | 16 | 24 | 4.1 |
| 127 | + | 6.5 | 6.5 | 0.62 | 12 | >100 | 7.4 | 8.5 | 2.9 | 3.9 |
| 128 | ++ | 9.5 | 5.0 | 0.39 | >100 | 85 | 12 | 5.9 | 7.6 | 1.9 |
| 37 | ++ | ND | ND | ND | ND | ND | ND | ND | ND | ND |
| 38 | NT$^e$ | NT | NT | NT | NT | NT | NT | NT | NT | NT |
| 45 | +++ | ND | ND | ND | ND | ND | ND | ND | ND | ND |
| 46 | +++ | ND | ND | ND | ND | ND | ND | ND | ND | ND |
| 55 | +++ | 1.8 | 0.92 | 1.5 | 1.1 | 3.9 | 2.9 | 3.6 | 0.88 | 0.13 |
| 56 | ++ | 0.48 | 0.24 | 0.33 | 0.27 | 0.22 | 0.31 | 0.34 | 0.34 | 0.10 |
| 63 | +++ | 0.40 | 0.30 | 0.34 | 0.57 | 0.54 | 0.94 | 0.26 | 0.30 | 0.21 |
| 64 | ++ | 3.0 | 4.1 | 2.5 | 3.5 | 1.7 | 6.3 | 2.6 | 3.6 | 0.60 |
| 65 | +++ | 0.11 | 0.054 | 0.074 | 0.078 | 0.052 | 0.14 | 0.057 | 0.051 | 0.024 |
| 66 | ++++ | 0.085 | 0.051 | 0.050 | 0.035 | 0.040 | 0.11 | 0.043 | 0.040 | 0.020 |

$^a$The relative Top1 inhibitory potencies of the compounds are presented as follows: 0: no detectable activity; +: weak activity; ++: similar activity as compound 2; +++ and ++++: greater activity than compound 2; ++++: similar activity as 1 μM 1.
$^b$Mean graph midpoint (MGM) for growth inhibition of all human cancer cell lines successfully tested.
$^c$The cytotoxicity GI$_{50}$ values listed are the concentrations corresponding to 50% growth inhibition, and are the result of single determinations.
$^d$GI$_{50}$s were not determined because the low activities revealed in the initial single-concentration testing at 10 μM did not warrant the multiple-concentration testing required for determination of GI$_{50}$ values.
$^e$Not tested.

The following publications are incorporated herein by reference: J. Med. Chem. 2011, 54, 6106-6166; J. Med. Chem. 2012, 55, 1682-1697.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A compound of the formula

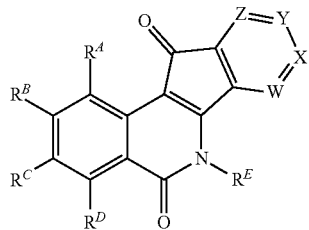

or a pharmaceutically acceptable salt thereof, wherein:
  each of $R^A$, $R^B$, $R^C$ and $R^D$ is independently hydrogen, hydroxy, acyloxy, halo, cyano, nitro, optionally substituted (1-6C) alkyl or optionally substituted (1-6C) alkoxy; or two adjacent $R^A$, $R^B$, $R^C$ and $R^D$ radicals form a methylenedioxy or ethylenedioxy group and each of the others is defined as above;
  $R^E$ is —(CH$_2$)$_n$R$^N$;
  n is 2, 3 or 4;
  $R^N$ is 1-imidazolyl, 1,2,4-triazol-2-yl or azido; or $R^N$ is —NR$^1$R$^2$; in which each of R$^1$ and R$^2$ is independently hydrogen or (1-3C) alkyl or in which one of R$^1$ and R$^2$ is methyl and the other of R$^1$ and R$^2$ is 2-hydroxyethyl or methyl; or —NR$^1$R$^2$ forms a pyrrolidino, piperidino, piperazino, morpholino or thiomorpholino group, each of which may bear one or more methyl substituents; in which a pyrrolidino or piperidino may bear a hydroxy substituent on a carbon not bound to nitrogen; and in which a pyrrolidino or piperidino may be a 3,4-didehydro moiety;
  W is N or CR$^W$; X is N or CR$^X$; Y is N or CR$^Y$; Z is N or CR$^Z$;
  one of W, X, Y and Z is N, and each of the others of W, X, Y and Z is CR$^W$, CR$^X$, CR$^Y$ or CR$^Z$, respectively; and
  each of R$^W$, R$^X$, R$^Y$ and R$^Z$, is independently hydrogen, (1-3C) alkyl, (1-3C) alkoxy, or acyloxy.

2. The compound of claim 1 wherein each of $R^A$ and $R^D$ is hydrogen.

3. The compound of claim 2 wherein each of $R^B$ and $R^C$ is methoxy, or $R^B$ is hydrogen and $R^C$ is nitro.

4. The compound of claim 1 wherein n is 3 and $R^N$ is dimethylamino or morpholino.

5. The compound of claim 1 wherein each of R$^W$, R$^X$ and R$^Z$ is hydrogen; and R$^Y$ is hydrogen or methoxy.

6. The compound of claim 1 wherein W is N.

7. The compound of claim 2 wherein W is N.

8. The compound of claim 3 wherein W is N.

9. The compound of claim 4 wherein W is N.

10. The compound of claim 5 wherein W is N.

11. The compound of claim 1 wherein X is N.

12. The compound of claim 1 wherein Y is N.

13. The compound of claim 1 wherein Z is N.

14. A pharmaceutical composition comprising a compound of claim 1, or a pharmaceutically acceptable salt thereof, together with a diluent, excipient or carrier.

15. A method of treatment of cancer comprising administering a therapeutically effective amount of a compound of claim 1, or a pharmaceutically acceptable salt thereof, to a patient in need thereof.

16. The method of claim 15 wherein the cancer is ovarian cancer, small-cell lung cancer, cervical cancer, colon cancer or rectal cancer.

17. A process for the preparation of a compound as described in claim 1, or a pharmaceutically acceptable salt thereof, comprising one or more of the steps of the group consisting of:

a. treating a homophthalic anhydride of the formula (A)

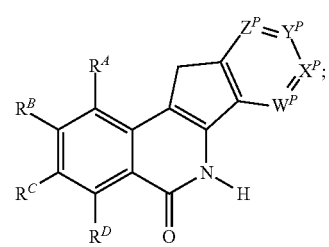

(A)

with a cyanopyridine of formula (B)

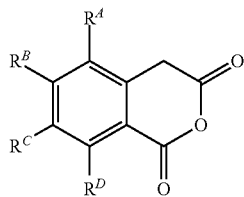

(B)

to form a compound of formula (C)

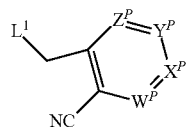

(C)

b. oxidizing a compound of formula (C), to afford a compound of formula (D)

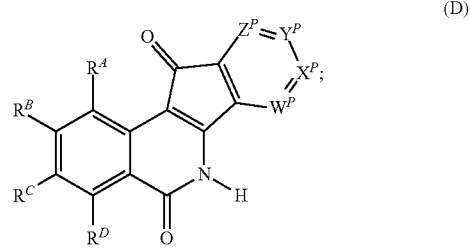

(D)

c. alkylating a compound of formula (D) with a compound of formula $R^E$-$L^2$; to afford a compound of claim 1; and d. alkylating a compound of formula H—$R^N$ with a compound of formula (E)

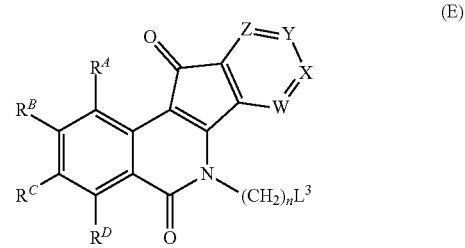

(E)

to afford a compound of claim 1; wherein
each of n, W, X, Y, Z, $R^A$, $R^B$, $R^C$, $R^D$ and $R^N$ is defined as in claim 1;
$W^P$ is N or $CR^{WP}$; $X^P$ is N or $CR^{XP}$; $Y^P$ is N or $CR^{YP}$; $Z^P$ is N or $CR^{ZP}$;
one of $W^P$, $X^P$, $Y^P$ and $Z^P$ is N, and each of the others of $W^P$, $X^P$, $Y^P$ and $Z^P$ is $CR^{WP}$, $CR^{XP}$, $CR^{YP}$ or $CR^{ZP}$, respectively; and
each $R^{WP}$, $R^{XP}$, $R^{YP}$ and $R^{ZP}$ is independently hydrogen, (1-3C) alkyl or (1-3C) alkoxy, or is a precursor or protected derivative thereof; and
each of $L^1$, $L^2$ and $L^3$ is a leaving group.

18. A compound, or salt thereof, selected from the group consisting of a compound of formula (C)

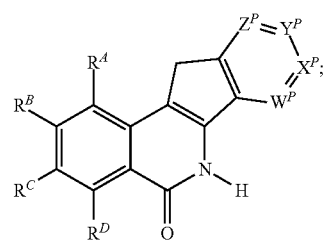

(C)

a compound of formula (D)

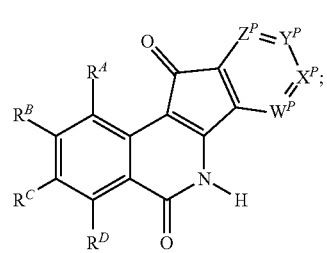

(D)

and
a compound of formula (E)

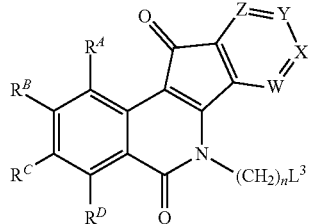

(E)

wherein
- $L^3$ is a leaving group;
- each of n, W, X, Y, Z, $R^A$, $R^B$, $R^C$ and $R^D$ is defined as in claim 1;
- $W^P$ is N or $CR^{WP}$; $X^P$ is N or $CR^{XP}$; $Y^P$ is N or $CR^{YP}$; $Z^P$ is N or $CR^{ZP}$;
- one of $W^P$, $X^P$, $Y^P$ and $Z^P$ is N, and each of the others of $W^P$, $X^P$, $Y^P$ and $Z^P$ is $CR^{WP}$, $CR^{XP}$, $CR^{YP}$ or $CR^{ZP}$, respectively; and
- each $R^{WP}$, $R^{XP}$, $R^{YP}$ and $R^{ZP}$ is independently hydrogen, (1-3)alkyl or (1-3C)alkoxy, or is a precursor or protected derivative thereof.

* * * * *